United States Patent [19]

Wilson et al.

[11] Patent Number: 5,612,211
[45] Date of Patent: Mar. 18, 1997

[54] STIMULATION, PRODUCTION AND CULTURING OF HEMATOPOIETIC PROGENITOR CELLS BY FIBROBLAST GROWTH FACTORS

[75] Inventors: Elaine L. Wilson; Janice Gabrilove, both of New York, N.Y.

[73] Assignees: New York University; Sloan-Kettering Institute For Cancer Research, both of New York, N.Y.

[21] Appl. No.: 76,875

[22] Filed: Jun. 15, 1993

Related U.S. Application Data

[63] Continuation-in-part of Ser. No. 950,549, Sep. 25, 1992, abandoned, which is a continuation-in-part of Ser. No. 536,108, Jun. 8, 1990, abandoned.

[51] Int. Cl.$^6$ ................................................. A61K 38/18
[52] U.S. Cl. ..................... 435/378; 435/377; 435/384; 514/2; 514/12; 530/324; 530/351; 530/399; 424/577; 435/325
[58] Field of Search ................................. 530/399, 324, 530/351; 424/577; 435/240.2, 240.21, 240.25; 514/2, 12

[56] References Cited

U.S. PATENT DOCUMENTS

| | | | |
|---|---|---|---|
| 4,296,100 | 10/1981 | Franco | 424/108 |
| 4,378,347 | 3/1983 | Franco | 424/108 |
| 4,642,120 | 2/1987 | Nevo | 623/16 |
| 4,785,079 | 11/1988 | Gospodarowicz | 530/399 |
| 5,198,356 | 3/1993 | Lieberman | 435/240.2 |
| 5,399,493 | 3/1995 | Emerson | 435/172.3 |
| 5,405,772 | 4/1995 | Ponting | 435/240.31 |

FOREIGN PATENT DOCUMENTS

| | | |
|---|---|---|
| 0281822 | 9/1988 | European Pat. Off. . |
| 0320148 | 6/1989 | European Pat. Off. . |
| 8900198 | 1/1989 | WIPO ............. C12N 15/00 |
| 9118620 | 12/1991 | WIPO . |
| 9211355 | 7/1992 | WIPO ............. C12N 5/02 |

OTHER PUBLICATIONS

Basilico, C., et al, "The FGF Family of Growth Factors and Oncogenes", *Advances In Cancer Research*, vol. 59, pp. 115–165, 1992.
*Illustrated Stedman's Medical Dictionary*, 24th ed., Williams and Wilkins, Baltimore, p. 860.
Nienhuis, A.W., M.D., "Hematopoietic Growth Factors", *The New England Journal Of Medicine*, vol. 318, pp. 916–918, 07 Apr. 1988.
Cosman, D., "Colony–stimulating Factors in vivo and in vitro", in News and Features section of *Immunology Today*, vol. 9, No. 4, pp. 97–98, 1988.
Mauch, P., et al., "Loss of Hematopoietic Stem Cell Self–Renewal After Marrow Transplantation", *Blood*, vol. 74, No. 2, pp. 872–875, 01 Aug. 1989.
Gospodarowicz, D., et al., "Fibroblast Growth Factor: Structural and Biological Properties", *J. Of Cellular Physiology Supplement*, vol. 5, pp. 15–26, 1987.

Metcalf, D., "The Granulocyte–Macrophage Colony–Stimulating Factors", *Science*, vol. 229, pp. 16–22, 05 Jul. 1985.
Sporn, M. B., et al., "Peptide growth factors are multifunctional", *Nature*, vol. 332, pp. 217–219, 17 Mar. 1988.
Goustin, et al., *Cancer Research*, vol. 46, pp. 1015–1029, 1986.
Mansukhani, A., et al, "Characterization of the murine BEK fibroblast growth factor (FGF) receptor: Activation by three members of the FGF family and requirement for heparin", *Proc. Natl. Acad. Sci. USA*, vol. 89, pp. 3305–3309, Apr. 1992.
Abboud, S.L., et al, "Peptide Growth Factors Stimulate Macrophage Colony–Stimulating Factor in Murine Stromal Cells", *Blood*, vol. 78, No. 1, pp. 103–109, 01 Jul. 1991.
Brockbank, K.G.M., et al, "Hemopoiesis on Purified Bone–marrow–derived Recticular Fibroblasts in vitro", *Exp. Hematol.*, vol. 14, pp. 386–394, 1986.
Gabbianelli, M., et al, "'Pure' Human Hematopoietic Progenitors: Permissive Action of Basic Fibroblast Growth Factor", *Science*, vol. 249, pp. 1561–1564, 28 Sep. 1990.
Gallicchio, V.S., et al, "Basic Fibroblast Growth Factor (B–FGF) Induces Early–(CFU–s) and Late–Stage Hematopoietic Progenitor Cell Colony Formation (CFU–gm, CFU–meg, and BFU–e) by Synergizing with GM–CSF, Meg–CSF, and Erythropoietin, and Is a Radioprotective Agent in Vitro", *International Journal of Cell Cloning*, vol. 9, pp. 220–232, 1991.
Brandt, et al., "Effect of Recombinant Human Granulocyte–Macrophage Colony–Stimulating Factor on Hematopoietic Reconstitution After High–Dose Chemotherapy and Autologous Bone Marrow Transplantation", *New Eng. J. Med.*, vol. 318, No. 14, pp. 869–876, 07 Apr. 1988.
Partanen, J., et al, "FGFR–4, A Novel Acidic Fibroblast Growth Factor Receptor with a Distinct Expression Pattern", *The EMBO Journal*, vol. 10, No. 6, pp. 1347–1354, 1991.
Thomas, K.A., "Fibroblast Growth Factors", *FASEB J.*, vol. 1, pp. 434–440, 1987.
Wilson, E.L., et al, "Basic Fibroblast Growth Factor Stimulates Myelopoiesis in Long–Term Human Bone Marrow Cultures", *Blood*, vol. 77, No. 5, pp. 954–960, 01 Mar. 1991.
Wang, Q.–R., et al, "Dissecting the Hematopoietic Microenvironment. VI. The Effects of Several Growth Factors on the in vitro Growth of Murine Bone Marrow CFU–F", *Experimental Hematology*, vol. 18, No. 4, pp. 341–347, May 1990.
Keegan, K., et al, "Isolation of an Additional Member of the Fiborblast Growth Factor Receptor Family, FGFR–3", *Proc. Natl. Acad. Sci. USA*, vol. 88, pp. 1095–1099, Feb. 1991.

(List continued on next page.)

*Primary Examiner*—Christina Y. Chan
*Assistant Examiner*—David Lukton
*Attorney, Agent, or Firm*—Browdy and Neimark

[57] ABSTRACT

Fibroblast growth factors are used in vivo, in situ and in vitro to stimulate stem cells, hemopoiesis, the immune system, transplant donor cells, culture and/or engraftment, wherein the use of fibroblast growth factors is disclosed for the stimulation of stem cells or hemopoietic cells, supporting cells and their progeny, in vitro, in situ and in vivo, as well as corresponding engrafting sites in vivo.

6 Claims, 16 Drawing Sheets

OTHER PUBLICATIONS

Abraham, J.A., et al, "Nucleotide Sequence of a Bovine Clone Encoding the Angiogenic Protein, Basic Fibroblast Growth Factor", *Science*, vol. 233, pp. 545–548, 01 Aug. 1986.

Abraham, J.A., et al, "Human Basic Fibroblast Growth Factor: Nucleotide Sequence and genomic Organization", *The EMBO Journal*, vol. 5, No. 10, pp. 2523–2528, 1986.

Brunner, G., et al, "Basic Fibroblast Growth Factor Expression in Human Bone Marrow and Peripheral Blood Cells", *Blood*, vol. 81, No. 3, pp. 631–638, 01 Feb. 1993.

Brunner, G., et al, "Phospholipase C Release of Basic Fibroblast Growth Factor from Human Bone Marrow Cultures as a Biologically Active Complex with a Phosphatidylinositol–anchored Heparan Sulfate Proteoglycan", *The Journal Of Cell Biology*, vol. 114, No. 6, pp. 1275–1283, Sep. 1991.

Moscatelli, "Fibroblast Growth Factors", *Cytokines Of The Lung*, Kelly, ed., Marcel Dekker, Inc., New York, pp. 41–76, 1992.

Florkiewicz, R.Z., et al, "Human Basic Fibroblast Growth Factor Gene Encodes Four Polypeptides: Three Initiate Translation From Non–AUG Codons", *Proc. Natl. Acad. Sci. USA*, vol. 86, pp. 3978–3981, Jun. 1989.

Huang, S., et al, "Formation of Haematopoietic Microenvironment and Haematopoietic Stem Cells From Single Human Bone Marrow Stem Cells", *Nature*, vol. 360, No. 24, pp. 745–749, 31 Dec. 1992.

Matsui, Y., et al, "Derivation of Pluripotential Embryonic Stem Cells from Murine Primordial Germ Cells in Culture", *Cell*, vol. 70, pp. 841–847, 04 Sep. 1992.

Olwin, B.B., et al, "Repression of Myogenic Differentiation by aFGF, bFGF, and K–FGF Is Dependent on Cellular Heparan Sulfate", *The Journal Of Cell Biology*, vol. 118, No. 3, pp. 631–639, Aug. 1992.

Olwin, B.B., et al., "Cell Surface Fibroblast Growth Factor and Epidermal Growth Factor Receptors Are Permanently Lost during Skeletal Muscle Terminal Differentiation in Culture", *The Journal Of Cell Biology*, vol. 107, pp. 761–769, Aug. 1988.

Prats, H., et al, "High Molecular Mass Forms of Basic Fibroblast Growth Factor are Initiated by Alternative CUG Codons", *Proc. Natl. Acad. Sci. USA*, vol. 86, pp. 1836–1840, Mar. 1989.

Resnick, J.L., et al, "Long–Term Proliferation of Mouse Primordial Germ Cells in Culture", *Nature*, vol. 359, pp. 550–551, 08 Oct. 1992.

Rossant, J., "Immortal Germ Cells?", *Current Biology*, vol. 3, No. 1, pp. 47–50, 1993.

Stemple, D.L., et al, "Isolation of a Stem Cell for Neurons and Glia from the Mammalian Neural Crest", *Cell*, vol. 71, pp. 973–985, 11 Dec. 1992.

Wolswijk, G., et al, "Cooperation Between PDGF and FGF Converts Slowly Dividing 0–2A$^{adult}$ Progenitor Cells to Rapidly Dividing Cells with Characteristics of 0–2A$^{perinatal}$ Progenitor Cells", *The Journal Of Cell Biology*, vol. 118, No. 4, pp. 889–900, Aug. 1992.

Flaumenhaft, R., et al., "Role of Extracellular Matrix in the Action of Basic Fibroblast Growth Factors: Matrix as a Source of Growth Factor for Long–Term Stimulation of Plasminogen Activator Production and DNA Synthesis", *J. Cell. Physiol.*, vol. 140, pp. 75–81, 1989.

Rifkin, D.B., et al, "Recent Developments in the Cell Biology of Basic Fibroblast Growth Factor", *J. Cell Biology*, vol. 109, pp. 1–6, Jul. 1989.

Olwin, B.B., et al., "Fibroblast Growth Factor Receptor Levels Decrease during Chick Embryogenesis", *J. Cell Biology*, vol. 110, pp. 503–509, Feb. 1990.

Ray, J., et al., "Proliferation, differentiation, and long–term culture of primary hippocampal neurons", *Proc. Nat'l Acad. Sci. USA*, vol. 90, pp. 3602–3606, Apr. 1993.

Metcalf, D., et al., "Proliferative Effects of Purified Granulocyte Colony–Stimulating Factor (G–CSF) on Normal Mouse Hemopoietic Cells", *J. Cell. Physiol.*, vol. 116, pp. 198–206, 1983.

Dorshkind, K., "Regulation of Hemopoiesis by Bone Marrow Stromal Cells and Their Products", *Ann. Rev. Immunol.*, vol. 8, pp. 111–137, 1990.

Dorshkind, K., et al., "Generation of purified stromal cell cultures that support lymphoid and myeloid precursors", *J. Immunol. Meth.*, vol. 89, pp. 37–47, 1986.

Gospodarowicz, D., et al., "Factors Involved in the Modulation of Cell Proliferation In Vivo and In Vitro: the Role of Fibroblast and Epidermal Growth Factors in the Proliferative Response of Mammalian Cells", *In Vitro*, vol. 14, No. 1, pp. 85–118, 1978.

Gospodarowicz, D., "Biological Activity In Vivo and In Vitro of Pituitary and Brain Fibroblast Growth Factor", *Mediators In Cell Growth And Differentiation*, Ford et al., eds., Raven Press, New York, pp. 109–134, 1985.

Gospodarowicz, D., et al., "Structural Characterization and Biological Functions of Fibroblast Growth Factor", *Endocr. Rev.*, vol. 8, No. 2, pp. 95–114, 1987.

Moscatelli, D., "Metabolism of Receptor–bound and Matrix–bound Basic Fibroblast Growth Factor by Bovine Capillary Endothelial Cells", *J. Cell Biol.*, vol. 107, pp. 753–759, Aug. 1988.

Dexter, T.M., et al., "Long–Term Marrow Culture: An Overview of Techniques and Experience", *Long–Term Bone Marrow Culture*, Alan R. Liss, Inc., pp. 57–96, 1984.

Fafeur, V., et al., "Basic FGF Treatment of Endothelial Cells Down–regulates the 85–KDa TGFβ Receptor Subtype and Decreases the Growth Inhibitory Response to TGF–β1", *Growth Factors*, vol. 3, pp. 237–245, 1990.

Nicola, N.A., "Hemopoietic Growth Factors and Their Interactions With Specific Receptors", *J. Of Cellular Physiology Supplement*, vol. 9, pp. 9–14, 1987.

Chang, J., et al., "Reconstitution of Haemopoietic System With Autologous Marrow Taken During Relapse of Acute Myeloblastic Leukaemia and Grown in Long–Term Culture", *The Lancet*, pp. 294–295, 08 Feb. 1986.

Clark, S. C., et al., "The Human Hematopoietic colony–Stimulating Factors", *Science*, vol. 236, pp. 1229–1237, 05 Jun. 1987.

Coulombel, L., M.D., et al., "Long–Term Marrow Culture Reveals Chromosomally Normal Hematopoietic Progenitor Cells in Patients with Philadelphia Chromosome–Positive Chronic Myelogenous Leukemia", *The New England Journal Of Medicine*, vol. 308, No. 25, pp. 1493–1498.

Coulombel, L., M.D., et al., "Long–Term Marrow Culture of Cells from Patients with Acute Myelogenous Leukemia", *J. Clin. Invest.*, vol. 75, pp. 961–969, Mar. 1985.

*Illustrated Stedman's Medical Dictionary*, 24th ed., Williams and Wilkins, Baltimore, p. 945, 1982.

Faseb Journal, 3:9 (1989), Bethesda, MD US.

Oliver, et al., Long Term Culture of Human Bone Marrow Stromal Cells in the Presence of Basic Fibroblast Growth Factor; *Growth Factors*, 3:P231–236 (1990).

Sonoda, et al., Analysis in serum–free culture of the targets of recombinant human hemopoietic growth factors: Interleukin 3 and granulocyte/macrophage–colony–stimulating factor are specific for early developmental stages; *Proc. Natl. Acad. Sci. USA* 85:4360–4364 (1988).

F I G. 10 a
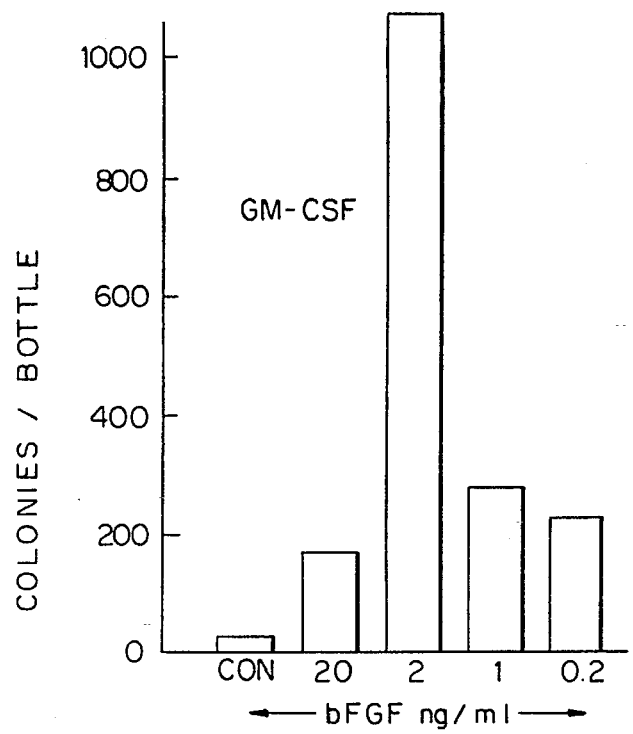
F I G. 10 b
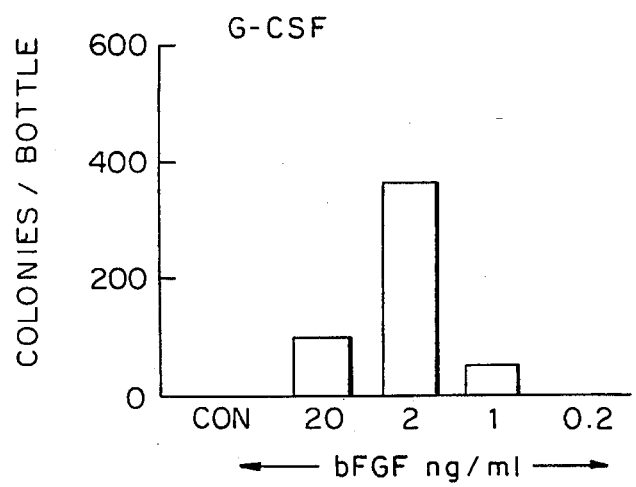
F I G. 10 c
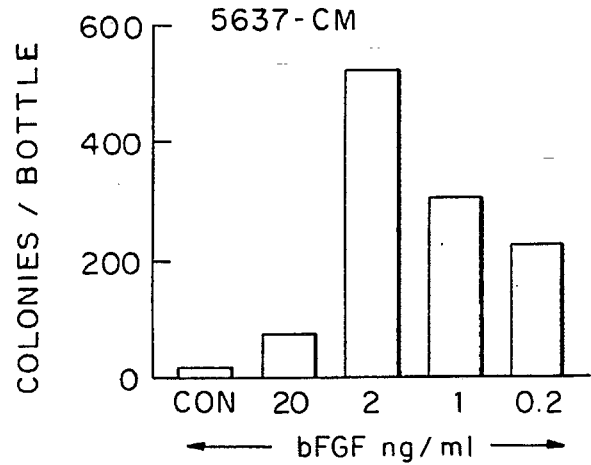

* $p < .001$ 1. bFGF = 100 ng/ml; SCF = 100 ng/ml; GM-CSF = 20 ng/ml

* p <.001

1. bFGF = 100 ng/ml; SCF = 100 ng/ml; GM-CSF = 20 ng/ml

STIMULATION, PRODUCTION AND CULTURING OF HEMATOPOIETIC PROGENITOR CELLS BY FIBROBLAST GROWTH FACTORS

This is a continuation of each of U.S. patent application Ser. No. 07/950,549, filed Sep. 25, 1992, now abandoned, the entire contents of which application is herein incorporated by reference. U.S. patent application Ser. No. 07/950, 549 is a continuation-in-part of, and entirely incorporates, U.S. Ser. No. 07/536,108, filed Jun. 8, 1990, now abandoned.

This invention was made under NIH Grant Number 5 NO1 CA 49419-03.

1. Field of the Invention

The present invention, in the field of cell biology and medicine, relates to the use of fibroblast growth factors for the stimulation of growth, differentition or culture of stem cells of all tissue types derived from embryonic stem cells or their progeny, such as hemopoietic progenitor and stem cells, supporting cells and their progeny, in vitro, in situ and in vivo, as well as corresponding engrafting sites in vivo, for use in diagnositic, therapeutic and research applications.

2. Background of the Invention

Cells in the body are replaced over a period of several days up to many months. The presence of stem cells of various tissue types are present to grow and differentiate as a source of replacement cells for those cells that die.

For example, the majority of blood cells are destined to die within a period of hours to weeks, depending on the specific blood cell type, and so must be continuously replaced. Hematopoietic stem cells are present at about 0.01% of the bone marrow and serve as a source of replacement blood cells. Many blood cell types can be produced from such stem cells as lymphoid and myeloid cells, such as erythrocytes, neutrophils, eosinophils, basophils, mast cells, monocytes and tissue macrophages, as well as osteoclasts, dendritic cells, Langerhans cells, Kupfer cells and T and B lymphocytes. Hematopoietic stem cells also differentiate into stromal cells which function in the formation and makeup of the hematopoietic microenvironment which supports growth and differentiation of hematopoietic stem cells into various types of lymphoid and myeloid cells under the control of cytokines. Cytokines are thus involved in controlling the specific growth and differentiation of hematopoietic stem cells into the specific blood cell types.

Cytokines are protein growth factors that function as intercellular signals that may regulate viabilty, growth and differentiation of hematopoietic cells, as well as local and/or systemic inflammatory responses, and include colony stimulating factors, interleukins and other growth factors having such activity. Interleukins were initially discovered and defined as proteins produced by leukocytes that affect leukocytes or other target cells. An interleukin designation is assigned to any protein that fulfills this definition. However, additional proteins fit the classification as an interleukin, but were named before this classification, such that the term cytokine is now used as the general term.

Cytokines that are produced by lymphocytes are termed lymphokines, whereas cytokines produced by monocytes or macrophages are given the term monokines. Thus, the terms cytokines, lymphokines, and interleukins may be used interchangeably to designate those peptide molecules that modulate host responses to foreign antigens or host injury by regulating the growth, mobility and differentiation of leukocytes and other cells.

Known cytokines include interleukins (IL) IL-1 (also known as endogenous pyrogen (EP), lymphocyte activating factor (LAF), mononuclear cell factor, catabolin, osteoclast activating factor and hematopoetin 1), IL-2 (also known as T cell growth factor (TCGF)), IL-3 (also known as multicolony stimulating factor (Multi-CSF), P-cell stimulating factor, WEHI-3B factor, mast-cell growth factor and histamine-producing factor), IL-4 (also known as B-cell growth factor (BCGF) and B-cell stimulatory factor-1 (BSF-1)), IL-5 (also known as T-cell replacing factor (TRF), B-cell growth factor II (BCGF-II), and eosinophil differentiation factor (EDF)), IL-6 (also known as interferon-$\beta_2$ (IFN-$\beta_2$), B-cell stimulating factor 2 (BSF-2), 26-kDa protein, hybridoma/plasmacytoma growth factor (HPGF or IL-HP-2), hepatocyte stimulating factor (HSF), and T-cell activating factor (TAF)), IL-7, IL-8 (also known as neutrophil activiating protein 1 (NAP-1)), IL-10 (also known as cytokine synthesis inhibitory factor (CSIF)), and IL-11; tissue necrosis factors (TNF) TNF$\alpha$ (also lymphotoxin (LT) and TNF$\beta$ (also known as macrophage derived TNF); interferons (IFN) IFN$\alpha$ and IFN$\beta$ (also known as type I IFN) and IFN$\gamma$ (also known as type II IFN) and tissue growth factor (TGF) $\beta$. The colony-stimulating factors (CSFs) (e.g., GM-CSF, G-CSF, M-CSF and IL-3) are specific glycoproteins that are thought to be involved in the production, differentiation, and function of hemopoietic stem cells into myeloid and lymphoid stem cells and their progeny.

Cytokines modulate target cells by interacting with cytokine receptors on the target cell. Principal cell sources of cytokines in vivo include T lymphocytes, B lymphocytes, macrophages, stromal cells, monocytes, leukocytes, and platelets. While cytokine specific receptors are specific for a given cytokine, cytokine receptors are grouped into families based on shared features. The first group of cytokine receptors is the hemopoetin group which are present on cells including immune system cells that bind IL-2, IL-3, IL-4, IL-6 and IL-7. A second receptor family is the TNF receptor family which bind both TNF$\alpha$ and TNF$\beta$. A third family is the immunoglobulin (Ig) superfamily receptor family, which contain an Ig sequence-like motif and includes human IL-1 and IL-6 receptors. See, e.g., Dawson, In Lymphokines and Interleukins (Dawson, ed.) CRC Press, Boca Raton, Fla. (1991); Mosmann et al, *Immunol. Rev.* 123: 209–229 (1991); Mosmann et al, *Immunol. Today* 12:A59–A69 (1991); Sherry et al, *Curr. Opinion Immunol.* 3:56–60 (1991); Paul, *Blood* 77:1859–1870 (1991); Dower et al, *J. Clin. Immunol.* 10:289–299 (1990); and (IL-11) Kawashima et al., *Nippon Rinsho* 50(8):1833–9 (1992).

Hemopoietic stem cells are a class of cells which have been defined functionally by the characteristics of extended self-renewal and the capacity to mature into one or more differentiated forms of blood cells, such as granulocytes, monocyte/macrophages, lymphocytes, erythrocytes, and megakaryocytes (which give rise to platelets) and stromal cells. In vitro, stem cells have proliferative capacity. The progeny of stem cells include, but are not limited to, the following.

A pluri-potent hemopoietic stem cell can differentiate into either a lymphoid stem cell or a myeloid stem cell. The lymphoid stem cell can differentiate into a B-cell progenitor or a T-cell in the thymus. The B-cell progenitor formation is induced by IL-7 or differentiation factors, and is inhibited by TGF$\beta$ or IL-4. The B-cell progenitor cell can further differentiate into a B-cell. The lymphoid stem cell can also differentiate into a T-cell progenitor cell which moves to the thymus. The T-cell progenitor can then be differentiated into a pre-T-cell, followed by differentiation into a specific T-cell.

Myeloid stem cells may differentiate into a burst-forming unit-erythroid followed by a colony forming unit-erythroid or by further differentiation into a red blood cell induced by erythropoietin. Alternatively, a myeloid stem cell can differentiate into a colony forming unit-megakaryocyte followed by differentiation into a megakaryocyte which can then form platelets.

Myeloid stem cells can also differentiate into a colony forming unit eosinophil (CFU-E) or a colony forming unit basophil (CFU-B) which can then differentiate into eosinophils or basophils, respectively, under the control of GM-CSF/IL-3 or IL-3, respectively. Supporting cells of the hemopoietic bone marrow cells, such as stromal cells, can secrete multiple cytokines with effects on the growth and/or differentiation of lymphoid and myeloid progenitor cells. In addition, other cytokines operative within the cytokine network can bind to stem cell growth supporting stromal cells and influence the types and concentrations of growth and/or differentiation factors secreted by the stromal cells, such as CSFs.

The various hemopoietic progenitor cell progeny, as described above, have specific CSF receptors which bind CSFs and mediate events in these cells which lead to specific differentiation pathways. Each CSF binds to a single class of high affinity receptors with no CSF being able to directly cross-react with another CSF's binding site. See, e.g., Metcalf, *Science* 254:529–533 (1991); Morstyn and Burgess, *Cancer* Research 48:5624–5637 (1988); Dorshkind, *Annu. Rev. Immunol.* 8:1–37 (1990); Nicola, *J. Cell. Physiol.*, Supplement, 5:9–14 (1987); Clark and Kamen, *Science* 236:1229–1237 (5 Jun. 1987).

The establishment of a cell culture system for the clonal development of hematopoietic cells has made it possible to discover the proteins that regulate cell viability, growth and differentiation of different hematopoietic cell lineages and the molecular basis of normal and abnormal cell development in blood-forming tissues. These regulators include cytokines such as colony stimulating factors and interleukins. Different cytokines can induce cell viability, multiplication and differentiation. Hematopoiesis is controlled by a network of interactions between these cytokines. This network includes positive regulators such as colony stimulating factors and interleukins and negative regulators such as transforming growth factor beta and tumor necrosis factor. Gene cloning has shown that there is a family of different genes for these cytokines. The functioning of the network requires an appropriate balance between positive and negative regulators and the selective regulation of programmed cell death (apoptosis).

There are different ways of inducing or inhibiting programmed cell death, and differences in the regulation of this program can result in tumor promotion or tumor suppression. The cytokine network which has arisen during evolution allows considerable flexibility, depending on which part of the network is activated and the ready amplification of response to a particular stimulus. A network may also be necessary to stabilize the whole system. Cytokines that regulate hematopoiesis can induce the expression of genes for transcription factors and can thus ensure the autoregulation and transregulation of cytokine genes that occur in the network. Sachs, *Int. J. Cell. Cloning* 10(4): 196–204 (1992).

The discovery of cytokines and their functions has involved the use of the study of cells in tissue culture which cells are modulated by cytokines. The culture of such cells has also provided a means for maintaining various cytokine modulated cell types in culture for relatively long periods of time.

For example, tissue culture techniques have been developed that permit maintenance of hemopoietic cells in vitro (Dexter, *Acta Haemat.* 62:299–305 (1979)). A vital component of this culture system is the prior formation of a bone marrow-derived adherent stromal cell layer in the culture vessel. The stromal layer consists of endothelial cells, fibroblasts, adipocytes, and macrophages (Weiss *J. Morphol.* 117:467–538 (1965); *Lichtman Exp. Hematol.* 9:391–410 (1981)). Different culture conditions enable selective proliferation of cells of the B lymphocyte (Whitlock et al., *J. Immunol. Methods* 67:353–369 (1984) or myeloid (Dexter et al., *J. Cell. Physiol.* 91:335–344 (1977)) cell lineage in stromal cell-dependent long term cultures. Certain cytokines such as IL-1 and IFN-γ have been shown to increase the production of various factors by adherent cells which may promote cell proliferation or differentiation (Zucali, et al., *J. Clin. Invest.* 77:1857–1863 (1986); Philip et al., *Nature* 323:86–89 (1986)). Little is known about the effects of other lymphokines on human bone marrow stromal cells, partly because it has been difficult to obtain large quantities of these cells.

Bone marrow transplantation is an increasingly common form of therapy for a number of diseases which involve dysfunction of hemopoietic cells (e.g., aplastic anemia), or which include treatments which irreversibly damage hemopoietic cells (for example chemotherapy and radiotherapy for cancer). Due to clinical problems related to imperfect matching of donors and recipients, autologous bone marrow transplantation, where the patient serves as his own donor, is preferable when possible, but requires an adequate number of stem cells to ensure success.

Autologous bone marrow transplantation may involve the removal of either peripheral blood stem cells, or less than 5% of the total content of the recipient bone marrow, which removed stem cells are stored frozen and reinfused for treatment. Mauch et al. (*Blood* 74:872–825 (1989)), studying animal transplant models, found a decrease in stem cell content and self-renewal capacity of bone marrow in transplant recipients that was proportional to the dose of transplanted bone marrow cells. This decrease (not reflected in peripheral blood leukocyte counts or bone marrow cellularity) was observed after initial bone marrow recovery, and did not change with time after transplantation, demonstrating a permanent loss in bone marrow regeneration capacity.

Myelosuppression (a suppression of blood cell elements derived from the bone marrow) is a common and serious complication of cancer therapy because most chemotherapeutic agents lack specificity for malignant cells, and bone marrow stem cells and other immature blood cells are particularly susceptible to damage from chemotherapeutic drugs and radiation. A major cause of treatment-related deaths in cancer patients is infection, which is a function of both the duration and the severity of neutropenia.

The use of autologous bone marrow and peripheral blood stem cell transplantation has allowed more intensive, and thus effective, chemotherapy and radiotherapy for a variety of neoplasms. However, morbidity and mortality can be high during the period required for engraftment and hemopoietic reconstitution.

Myelosuppression can also occur following administration of antibiotics, antidepressants, nonsteroidal anti-inflammatory drugs, anti-viral agents, and/or following treatment of thyroid disease. Myelosuppression also accompanies a variety of immunosuppressive disorders, such as AIDS.

Brandt et al. (*New Eng. J. Med.* 318:869–876 (1988)), describe the use of recombinant human granulocyte-macrophage colony-stimulating factor (GM-CSF) for hemopoietic reconstitution after high-dose chemotherapy and autologous bone marrow transplantation and found accelerated myeloid recovery over a range of tolerable GM-CSF doses.

Fibroblast Growth Factors (FGFs)

Many peptides with potent stimulatory effects on proliferation of either epithelial or mesenchymal cells have been identified. Because of their regulatory action on tissue growth, these peptides have been collectively termed "growth factors." Furthermore, many disparately named factors have, upon purification, turned out to be a single molecular entity.

Fibroblast growth factors (FGFs) include, but are not limited to, basic and acidic FGF, (Int-2), (hst/K-FGF), FGF-5, FGF-6 and keratinocyte growth factor (KGF). All fibroblast growth factors bind to the same family of receptors. For example, Moscatelli (in Kelley, ed., *Cytokines of the Lung*, Marcel Dekker, Inc., New York, pp 41–76 (1992)) discloses that five other polypeptides with amino acid sequence homology to basic and acidic FGF have been identified: keratinocyte growth factor and the products of the int-2, hst/K-fgf, FGF-5, and FGF-6 protooncogenes. These related molecules have mitogenic activity and also bind tightly to heparin affinity columns. These seven polypeptides constitute the FGF family and interact with overlapping affinities for the same family of receptors. The relationship of FGF receptors was partially resolved with the cloning and sequencing of the receptors.

Basilico et al, *Advances in Cancer Research* 59:115–165 (1992), discloses that the discovery of seven fibroblast growth factors, many of which seem to have a very similar spectrum of action, raises the question of what the evolutionary advantage for the organism could be in producing many growth factors with similar target specificity.

Mansukhani et al, *Proc. Nat'l Acad. Sci. USA* 89:3305–3309 (1992), discloses that fibroblast growth factors (FGFs) are a family of seven heparin-binding polypeptides that share a 30–40% homologyo Like other growth factors, FGFs act by binding and activating specific cell-surface receptors, and the FGF receptors also represent a family.

Rifkin et al. (*J. Cell Biology* 109:1–6 (1989)) discloses that bFGF is multifunctional in that it can stimulate proliferation and induce or delay differentiation. Basic FGF stimulates other critical processes in cell function as well, though the mechanisms of FGF's various actions have yet to be clarified.

FGFs differ from other growth factors such as epidermal growth factor (EGF), platelet derived growth factor (PDGF), colony stimulatory factors (CSFs) and interleukins, or TGFβ, by their amino acid sequence, their ability to stimulate proliferation of many non-hemopoietic cell types involved in wound healing, in vitro as well as in vivo. These cell types include capillary endothelial cells, vascular smooth muscle cells, fibroblasts, chondrocytes, and myoblasts.

FGF has been used for the treatment of ischemic heart disease (U.S. Pat. Nos. 4,296,100 and 4,378,347 to Franco), where it was found to increase blood flow in the heart for sustained periods of time after myocardial infarction.

Nevo et al. (U.S. Pat. No. 4,642,120) discloses the use of FGF for repairing defects of cartilage and bones.

Senoo et al. (European Patent Publication EP 281 822) discloses a mutein of bFGF which can be used to accelerate cell growth in vitro and can act as a healing accelerator for burns and a therapeutic drug for thrombosis.

Arakawa et al., European Patent Publication EP 320 148 discloses recombinant bFGF analogs which possess at least one of the biological properties of mammalian bFGF factor.

The bFGF appears to induce neovascularization, re-epithelization and wound repair.

Citation of the above documents is not intended as an admission that any of the foregoing is pertinent prior art. All statements as to the date or representation as to the contents of these documents is based on the information available to the applicant and does not constitute any admission as to the correctness of the dates or contents of these documents.

SUMMARY OF THE INVENTION

It is an object of the present invention to overcome one or more of the deficiencies in the related art.

It is a further object of the present invention to provide a method for the use of fibroblast growth factors for the stimulation of growth, differentiation or culture of stem cells generally, such as cells including and derived from mesenchymal stem cells, endodermal stem cells or ectodermal stem cells, stromal cells, other supporting cells, or their progeny, in vitro, in situ or in vivo.

It is another object of the present invention to provide a method for the use of a fibroblast growth factor for the stimulation of the growth and/or differentiation of hemopoietic stem cells, supporting cells and their progeny, in vitro, in situ and in vivo, as well as corresponding engrafting sites in vivo.

It is another object of the present invention to culture bone marrow, or peripheral blood, stromal cells and stem cells for use in bone marrow transplantation and/or stem cell and progenitor cell supplementation by stimulating stromal cell growth with a fibroblast growth factor in vitro, in situ and in vivo. For example, FGF-stimulated stem cells or their progeny, obtained from peripheral blood or the bone marrow, or other sources, (e.g., liver or spleen), may be used therapeutically to treat myelosuppression, e.g., associated with dose intensified chemotherapeutic regimens.

It is yet another object of the present invention to treat hemopoietic stem cells, in vitro, in vivo or in situ, with FGF, or a functional derivative thereof, to increase their differentiation and/or numbers for more effective bone marrow transplantation and/or in stem cell and progenitor cell supplementation.

It is a further object of the present invention to accelerate establishment of a bone marrow and/or a peripheral blood progenitor/stem cell graft and reconstitution of hemopoietic processes with bone marrow of a subject by administering to a bone marrow transplant recipient FGF polypeptide, or a functional derivative thereof, alone or in combination with one or more colony stimulating factors, wherein the stem cells and/or progenitor cells are obtained from peripheral blood or bone marrow.

It is still a further object of the present invention to provide combination therapy for regulating blood cell production and treating disease states caused by hemopoietic dysfunction (such as aplastic anemia, thrombocytopenia, neutropenia) or hyperplasia (such as various forms of myeloproliferative disease), as well as a general stimulant for the immune system, in vivo, in vitro and in situ, by the administration of a therapeutically effective amount of at least one FGF, optionally in combination with at least one colony stimulating factor.

It is still another object of the present invention to treat certain marrow aplastic or dysplastic conditions by stimulating endogenous cytokines using a therapeutically effective amount of at least one FGF or a functional derivative thereof, optionally in combination with a therapeutically effective amount of at least one CSF.

It is another object of the present invention to increase the concentration of stem cells in a bone marrow, or peripheral blood, stem cell donor prior to, during or after, transplantation, in order to increase the effectiveness of the engrafting of the transplanted stem cells into the bone marrow, by administering a therapeutically effective amount of an FGF or a functional derivative thereof, optionally in combination with a therapeutically effective amount of at least one CSF.

It is still another object of the present invention to provide a method for obtaining large numbers of bone marrow stromal cells that can be used to maintain cultures of hemopoietic cells and/or stem cells/progenitor cells for therapeutic and research purposes, according to the present invention.

Another object of the present invention is to provide a method for stimulating the growth and/or proliferation of hemopoietic progenitor cells, stem cells and/or stromal cells in vitro for use in animal or human subjects in vivo, such as for in vivo infusion for donor stimulation, transplantation or reimplantation of the cells.

It is another object of the present invention to culture a large number of stem cells for use in transplantation and/or stem cell and progenitor cell supplementation, by stimulating stem cell growth with a fibroblast growth factor in vitro, in situ and in vivo.

For example, FGF-stimulated stem cells or progenitor cells, obtained from an animal tissue sample or biopsy, may be used as a therapeutic composition to treat degenerative diseases by replacing or supplementing pathologic tissue with donor, optionally cultured, stem cells stimulated with at least one FGF, optionally with at least one additional growth factor, such as a CSF.

It is yet another object of the present invention to treat stem cells, in vitro, in vivo or in situ, with FGF, or a functional derivative thereof, to increase their numbers for more effective stem cell and/or progeny cell transplantation and/or supplementation.

It is a further object of the present invention to accelerate establishment of a stem cell/progeny graft and reconstitution of the tissue type provided by the stem cell/progeny graft of a subject, by administering to a stem cell/progeny transplant recipient an FGF, alone or in combination with one or more colony stimulating factors, wherein the stem/progenitor cells are obtained from a donor subject or the recipient, optionally cultured before administration.

It is still a further object of the present invention to provide combination therapy for treating disease states caused by, or involving, pathologies or cell or tissue derived from stem cells or progeny thereof, in vivo, in vitro and in situ, by the administration of a therapeutically effective amount of at least one FGF, optionally in combination with at least one colony stimulating factor.

It is another object of the present invention to increase the concentration of stem cells or progeny in a peripheral blood stem cell donor prior to, during or after, transplantation, wherein the donor can be the same or different from the recipient, in order to increase the effectiveness of the engrafting of the transplanted stem cells into the recipient by administering a therapeutically effective amount of an FGF or a functional derivative thereof, optionally in combination with a therapeutically effective amount of at least one CSF, to at least one of the donor or the recipient of the stem cell/progeny transplant.

It is still another object of the present invention to provide a method for obtaining an increased number of viable stem cells of ectodermal, mesodermal or endodermal origin by culturing that can be used to culture stem cells in the presence of a fibroblast growth factor, to provide such stem cells in sufficient quantities sufficient for for therapeutic and research purposes, according to the present invention.

Another object of the present invention is to provide a method for stimulating the growth and/or proliferation of stem cells of ectodermal, mesodermal or endodermal origin in vitro for use in animal subjects in vivo, such as for in vivo infusion for donor stimulation, transplantation or reimplantation of such stem cells or progenitor cells thereof.

Other objects, features and/or advantages of the invention will be apparent to skilled practitioners from the following detailed description and examples relating to the present invention.

BRIEF DESCRIPTION OF THE DRAWINGS

FIGS. 10a–10c are a set of bar graphs showing concentration-dependent stimulation of stem cell responses to CSF's by bFGF. Human bone marrow was seeded at $2\times10^7$ buffy coat cells/75 cm$^2$ flask in the absence and presence of 20, 2, 1, and 0.2 ng/ml bFGF. At various intervals, cells in the supernatant were harvested and seeded in soft agar in the absence or presence of one of several CSF's (GM-CSF, G-CSF, and 5637-CM) which stimulate the growth of cells of myeloid origin.

DETAILED DESCRIPTION OF THE INVENTION

Figure 1A:
FIGS. 1a–1d is a set of photomicrographs showing the effect of bFGF on the morphology of bone marrow (BM) stromal cells. Phase constant micrographs of stromal cultures at different densities in the absence FIG. 1A and FIG. 1C and in the presence FIG. 1B and FIG. 1D of 20 ng/ml of bFGF. The scale bar=50 µm.
Figure 1B:
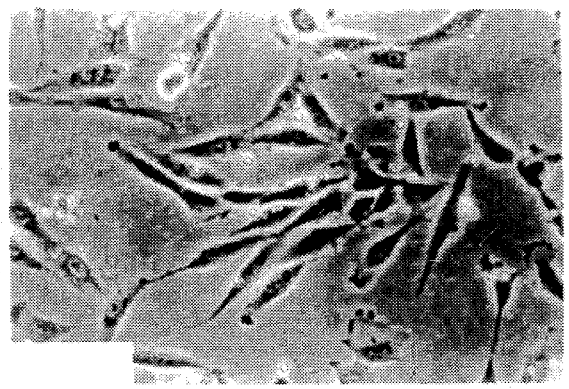

The present invention relates to the discovery that fibroblast growth factors (FGFs) can stimulate the growth, differentiation, engraftment and/or proliferation of stem cells generally, such as stem cells of endodermal, ectodermal or mesodermal origin, such as tissue, organ, progenitor cells, tissue specific stem cells, supporting stromal cells, and progeny thereof, found in cells or tissues of an animal, such as in organs, glands, tissue, e.g., bone marrow and/or in the peripheral blood, in vivo, in vitro and in situ. The stimulation of stromal cells may indirectly stimulate progenitor and/or stem cells by supporting growth of stem cells or hematopoietic cells associated therewith.

Accordingly, the term "stem cell" or "progeny thereof", in the context of the present invention, refers to any cell capable of further differentiation or development, from which further differentiation or development results in increased specialization or modification of the phenotype of the stem cell or tissue, or progeny thereof. Such stem cells are derived from cells, precursor cells or intermediate cells of mesodermal, endodermal or ectodermal origin, as described herein.

Furthermore, the present invention also relates to the discovery that myelopoiesis in bone marrow culture is stimulated by FGF, as well as culture of stem cells and progenitor cells generally, and their progeny such as granulocytes, monocytes, macrophages, lymphocytes, erythrocytes, megakaryocytes, cells and tissue of the central nervous system, such as nerve, glial, brain cells or tissue, liver cells, kidney cells, muscle cells, heart cells or myocardial cells, arterial or venous cells or tissue, eye cells, connective tissue or cells, lung tissue or cells, spleen cells or tissue, endocrine tissue or cells, premordial germ cells and their progeny, etc.

Furthermore, the present invention also relates to the additional discovery that FGF can potentiate the effects of colony stimulating factors and other cytokines, such as stem cell in vivo, in situ and/or in vitro.

Accordingly, the present invention relates in general to the discovery that FGFs stimulate the growth and stimulation and/or prevention of differentiation of stem cells of different types; such as hemopoiesis, primordial germ cells (see culturing of in Matsui et al., *Cell* 70:841 (1992) and Resnick et al., *Nature* 359:550 (1992)), myoblasts (see culturing in Olwin et al., *J. Cell Biol.* 107:761 (1988); Olwin et al., *J.*

*Cell Biol.* 110:503 (1990); and Olwin and Rapraeger *J. Cell Biol.* 118:631 (1992)), neural cells (see culturing in Stempel and Anderson *Cell* 71:973 (1992); Ray et al. *Proc. Nat'l Acad. Sci. USA.* 90:3602–3606 (1993)), in vivo, in vitro, and in situ. Non-limiting examples of such stem cells include, but are not limited to, cells including or derived from or precursors of, myogenic, macrophage, keratinocytes, embryonic, premordial germ cells, osteoblasts, osteoclasts, glial cells, adipose cells or tissue, intestinal epithelium, liver, heart, brain, nerve, dermal, spleen, lung, kidney, bone, lymph, ovary, thyroid, gall bladder, pancreas, pituitary, hypothalamus, cerebellum, cerebrum, pons, spinal cord, cartilage, ligment, tendon, muscle, cardial muscle, smooth muscle, small intestine, large intestine, colon, artery, vein, and the like.

By the term "hemopoiesis" is intended the production of cellular elements of the blood from hemopoietic progenitor and stem cells, initially as myeloid and lymphoid cells and their progeny, and further includes, but is not limited to, megakaryocytopoiesis, myelopoiesis, lymphopoiesis, eosinophilpoiesis, neutrophilpoiesis, T-cell production, B-cell production, platelet production, basophil production and erythropoiesis and monocyte production.

The terms "hemopoietic stem cell", "hematopoietic progenitor cell" or "hemopoietic bone marrow cell" refers to a cell in any of the blood cell lineages (e.g., myeloid, monocytoid, basophil, neutrophil, erythroid, lymphoid, megakaryocytoid) which is a precursor of the mature blood or lymph cell or stromal cell. The term as used herein is intended to also include very early precursors, such as pluripotent stem cells which are both self-renewing and which give rise to all lineages and stromal cells, as well as committed stem cells which may have more limited self-renewal capacity than pluripotent stem cells, and are committed to a particular cell lineage.

Also, pluripotent stem cells are targets of the methods of the present invention. For example, myeloid stem cells which are thought to be derived from the committed stem cells of the myeloid lineage, are considered to be targets of the methods of the present invention, which may also include, but is not limited tog precursor cells of, or, red blood cells (RBCs), platelets, monocytes, neutrophils, and eosinophils. For a brief description of hematopoietic cell development/differentiation, see, e.g., Metcalf et al. *J. Cell. Physiol.* 116:198 (1983).

Additionally, FGFs can be used according to methods of the present invention to stimulate a subject's immune system, due to the fact that FGFs have been discovered to stimulate hemopoietic stem cells and progeny thereof, proliferation in vivo, in situ and in vitro, at preliminary stages of differentiation of hematopoietic cells.

FGFs are therefore expected to stimulate general increased proliferation, stimulation, growth and/or differentiation of blood cells and lymphocytic cells involved, e.g., in oxygen transport and cellular and humoral immunity, including, but not limited to; red blood cells (RBCs), platelets, leukocytes, white blood cells, neutrophils, eosinophils, basophils, monocytes and lymphocytes, monocytes, macrophages, T-lymphocytes and B-lymphocytes.

The term "fibroblast growth factor" or "FGF" includes any protein or polypeptide having FGF biological activity, such as binding to FGF receptors, which activity has been used to characterize various FGFs, including, but not limited to acidic FGF, basic FGF, Int-2, hst/K-FGF, FGF-5, FGF-6 and KGF. For a description of some examples and characteristics of previously known FGFs, see, e.g., Moscatelli, supra.

According to the present invention, the administration of an FGF can thus be used to stimulate proliferation of any of the above cell types in vitro, in situ and in vivo, for the purpose of transplant into a recipient, or for stimulating any physiological functions association with these cells, such as production of these cells. The presence and proliferative activity of stem cells may occur in any tissue, gland or organ containing the particular stem cell, or progeny thereof, of interest. An FGF may also be used according to the present invention in combination with one or more growth factors, such as cytokines, epidermal growth factor (EGF), platelet-derived growth factor (PDGF), insulin like growth factor-1 (IGF-1), transforming growth factor-$\beta$ (TGF-$\beta$), A non-limiting example of the presence and proliferative activity of hemopoietic stem cells is primarily in the bone marrow, but also occurs in, e.g., the peripheral blood. To the extent that extramedullary hemopoiesis occurs, it is intended to be within the scope of the present invention, such that FGFs have also been found to stimulate the growth of bone marrow stromal cells, as well as greatly accelerating the formation of a primary stromal cell layer following culture of freshly harvested bone marrow cells. In the presence of an FGF, such as bFGF, stromal cells attain high densities, lose their contact inhibition, and grow in multilayered sheets.

The term "stromal cell" refers to a heterogeneous population of cells naturally present in the bone marrow, but which can also be cultured or stimulated in vivo, in vitro and in situ. In culture, stromal cells grow in the form of an adherent layer. Stromal cells may include, as non-limiting examples, cells derived from the bone marrow which are referred to as at least one of adipocytes, preadipocytes, fibroblasts, fibroblast colony forming units (CFU-F), reticular cells and macrophages. Cloned stromal cell lines derived from such cells are also contemplated to be within the scope of the present invention (see, e.g., Dorshkind (*Ann. Rev. Immunol.* 8:111–137 (1990)), which is entirely incorporated herein by reference.

In the context of the present invention, hematopoietic progenitor cells, hematopoietic stem cells and supporting stromal cells and progeny thereof, are not intended to include osteoblasts, osteoclasts and chondrocytes or related cells. However, the term "stem cell" or "progeny thereof" is intended to include such bone or cartilage related stem cells, progeny thereof, as well as associated stromal cells.

Heparan sulfate is known to be a component of the extracellular matrix which influences hemopoiesis. Growth factors such as colony stimulating factors have been shown to bind to heparin, serving as a possible mechanism by which stromal cells affect hemopoiesis (see, e.g., Roberts et al., *Nature* 332:376–378 (1988)).

Heparin may be used according to the present invention to potentiate the stimulatory effect of concentrations of an FGF administered to a hematopoietic cell donor, recipient or subject according to a method of the present invention. For a description of bone marrow cell transplantation and related procedures, see, e.g., Saksela, O. et al., *J. Cell Biol.* 107:743–751 (1988); Ulrich et al. *Biochem. Biophys. Res. Commun.* 137:1205–1213 (1986); and Example 7 below. In addition to heparin, the use of a heparin related compounds, such as heparin analogs, fragments, synthetic heparin substitutes or modified heparins are intended within the scope of the present invention.

Heparin preparations may be nonuniform and heterogeneous in composition, molecular size, structure, position of substituents (N-sulfate, O-sulfate, and glucuronic acid), and sequence (Goldgaber et al., *Science* 235:877 (1987); Tanzi et al., *Science* 235:881 (1987); Robakis et al., *Proc. Natl. Acad. Sci. USA* 84:4190 (1987)). This heterogeneity is thought to be responsible for various effects observed.

Heparin can be modified, or heparin fragments synthesized by methods known in the art (Choay et al., *Biochem. Biophys. Res. Comm.* 116:492 (1983); van Boeckel et al., *Tetrahedron Lett.* 29:803 (1988), both of which references are entirely incorporated herein by reference).

Preferred heparin fragments include a hexasaccharide or a pentasaccharide fragment. Preferred synthetic heparin substitutes comprise cyclodextrins of six or eight glucopyranose units, such as, for example, β-cyclodextrin tetradecasulfate.

Cyclodextrins are naturally occurring cyclic nonreducing, water-soluble oligosaccharides built up from six to eight glucopyranose units (Bender et al., *Cyclodextrin Chemistry*, Springer Verlag, Berlin, 1978); Saenger, W., *Angew. Chem. Int. Ed. Engl.* 91:344 (1980); Saenger, In: *Inclusion Compounds* (Atwood et al., eds.), Academic Press, New York, 1984, vol. 2, pp. 232–259).

Therapeutic Administration and Compositions

The present invention provides therapeutic applications for treatment of animals, preferably humans for degenerative diseases or side effect of such diseases or their treatment by using at least one FGF to stimulate stem cells or their progeny in vivo, in vitro or in vitro, to provide increased numbers of such stem cells and their progeny which increased numbers provides a therapeutic effect on an animal. The increased numbers of stem cells or progeny of at least one particular stem cell and/or progeny can be provided by at least one of in vivo stimulation of such cells, in vitro growth of such cells and transplant or engraftment into the same or different animal providing the stem cells; optionally in combination or in further combination with treatment of the recipient prior and/or during transplant in order to enhance engraftment of such transplanted cells. Such stem cells and their progeny may include at least one cell of one or more tissues, organs or glands, or another cell useful for treating a pathology treatable by methods of the present invention involving FGF.

As non-limiting examples of diseases or pathologies treatable by methods of the present invention, neurodegenerative diseases, hepatodegenerative diseases, nephrodegenerative diseases, spinal cord injury, head trauma or surgery, viral infections which result in tissue, organ or gland degeneration, and the like.

Neurodegenerative diseases include, but are not limited to, AIDS dementia complex, demyelinating diseases, such as multiple sclerosis and acute transverse myelitis; extrapyramidal and cerebellar disorders, such as lesions of the corticospinal system; disorders of the basal ganglia or cerebellar disorders; hyperkinetic movement disorders such as Huntington's Chorea and senile chorea; drug-induced movement disorders, such as those induced by drugs which block CNS dopamine receptors; hypokinetic movement disorders, such as Parkinson's disease; progressive supra-nucleo palsy; structural lesions of the cerebellum; spinocerebellar degenerations, such as spinal ataxia, Friedreich's ataxia, cerebellar cortical degenerations, multiple systems degenerations (Mencel, Dejerine-Thomas, Shi-Drager, and Machado-Joseph); systemic disorders (Refsum's disease, abetalipoprotemia, ataxia, telangiectasia, and mitochondrial multi-system disorder); demyelinating core disorders, such as multiple sclerosis, acute transverse myelitis; and disorders of the motor unit, such as neurogenic muscular atrophies (anterior horn cell degeneration, such as amyotrophic lateral sclerosis, infantile spinal muscular atrophy and juvenile spinal muscular atrophy); Alzheimer's disease; Down's Syndrome in middle age; Diffuse Lewy body disease; Senile Dementia of Lewy body type; Wernicke-Korsakoff syndrome; chronic alcoholism; Creutzfeldt-Jakob disease; Subacute sclerosing panencephalitis Hallerrorden-Spatz disease; and Dementia pugilistica. See, e.g., Berkow et al, eds., *The Merck Manual*, 15th edition, Merck and Co., Rahway, N.J., 1987, which reference, and references cited therein, are entirely incorporated herein by reference.

Nephrodegenerative diseases include, but are not limited to, AIDS-associated nephropathy, immunologically related mediated renal diseases, glomerular diseases, tubulointerstitial disease, nephrotoxic disorders and hereditary chronic nephropathies. See, e.g., Berkow et al, eds., *The Merck Manual*, 15th edition, Merck and Co., Rahway, N.J., pp 1552–1633 and 1647–1648, 1987, which reference, and references cited therein, are entirely incorporated herein by reference.

According to another aspect of the present invention, at least one FGF is administered optionally in combination with at least one CSF and/or heparin, or analog thereof, to animal or human subjects to stimulate hemopoiesis (for example, in bone marrow transplant recipients) or to increase the number of stem cells, progenitor cells or stromal cells in donors or recipients before, during or after tiissue, organ, gland or bone marrow removal or transplantation. See, e.g., Berkow et al, eds., *The Merck Manual*, 15th or 16th edition, Merck and Co., Rahway, N.J., 1987, 1992; Goodman et al., eds., *Goodman and Gilman's The Pharmacological Basis of Therapeutics*, 8th edition, Pergamon Press, Inc., Elmsford, N.Y., (1990); *Avery's Drug Treatment: Principles and Practice of Clinical Pharmacology and Therapeutics*, 3rd edition, ADIS Press, LTD., Williams and Wilkins, Baltimore, Md. (1987), Ebadi, *Pharmacology*, Little, Brown and Co., Boston, (1985), which references and references cited therein, are entirely incorporated herein by reference.

A therapeutically effective amount of at least one FGF, optionally in combination with a therapeutically effective amount of at least one CSF and/or heparin, may be administered by any means that achieve its intended purpose, such as by oral or parenteral administration. For example, administration may be by various parenteral routes such as subcutaneous, intravenous, intradermal, intramuscular, intraperitoneal, intranasal, transdermal, intraarterial, intrathecal, or buccal routes.

Alternatively or additionally, administration may be by topical administration to the mucous membranes (e.g., of the conjunctiva, nasopharynx, oropharynx, vagina, colon, urethra, urinary bladder or nasal mucosa) or to the skin when a therapeutically effective amount of at least one FGF, optionally in combination with a therapeutically effective amount of at least one CSF and/or heparin, is applied in a lipid soluble vehicle. Alternatively, or concurrently, administration may be by pulmonary absorption, such as through the pulmonary epithelium or through the mucous membranes of the respiratory tract. See, e.g., Berkow, supra, Goodman, supra, Avery, supra and Ebadi, supra, which are entirely incorporated herein by reference, included all references cited therein.

Alternatively or concurrently, administration may be by oral route such as by oral ingestion or sublingual administration, as well as by rectal administration, e.g., as a suppository. Parenteral administration may be by bolus injection or by gradual perfusion over time. See, e.g., Berkow, supra, Goodman, supra, Avery, supra and Ebadi, supra, which are entirely incorporated herein by reference, including all references cited therein.

It is understood that the dosage of a therapeutically effective amount of at least one FGF, optionally in combination with a therapeutically effective amount of at least one CSF and/or heparin (as presented herein) may be administered in vivo, in situ, or in vitro will be dependent upon the age, sex, health, and weight of the recipient, type of concurrent treatment, if any, frequency of treatment, and the nature of the effect desired, depending on the route and formulation used for administration. The ranges of effective doses provided below are not intended to limit the invention and represent preferred dose ranges. However, the most preferred dosage will be tailored to the individual subject depending on the bioavailability of the FGF composition, comprising a therapeutically effective amount of at least one FGF, optionally in combination with a therapeutically effective amount of at least one CSF and/or heparin, used according to a method of the present invention, as is understood and determinable by one of skill in the art, based on appropriate determinations of chemical equivalency, biological equivalency and/or therapeutic equivalency, according to known method steps. See, e.g., Berkow, supra, Goodman, supra, Avery, supra and Ebadi, supra, which are entirely incorporated herein by reference, including all references cited therein.

Preparations comprising a therapeutically effective amount of at least one FGF, optionally in combination with a therapeutically effective amount of at least one CSF and/or heparin, for parenteral administration include sterile aqueous or non-aqueous solutions, suspensions, and emulsions, which may contain auxiliary agents or excipients which are known in the art. Pharmaceutical compositions such as tablets and capsules can also be prepared according to routine methods.

At least one FGF, optionally with at least one CSF and/or heparin, may be administered in a therapeutically effective amount to an animal to stimulate stem cells or progeny thereof in any tissue, gland or organ cell donor or recipient, prior to, during or after removal, culture, transplantation, or engraftment, in any amount which is sufficient to provide its intended purpose, preferably in the range of from about 0.01 µg/kg body weight to about 2.0 mg/kg body weight, such as 0.02, 0.05, 0.07, 0.09, 0.1, 0.3, 0.5, 0.7, 0.9, 1, 3, 5, 7, 9, 10, 20, 50, 70, 90 µg/kg or 0.1, 0.2, 0.5, 0.7, 0.9, 1, 1.5 or 2 mg/kg, or any range therein. When used in vitro to promote stromal cell or stem cell growth, the therapeutically effective amount of at least one FGF, optionally in combination with a therapeutically effective amount of at least one CSF and/or heparin, is preferably added to the medium to achieve a final concentration of about 0.01 µg\L to 2.0 mg\L.

A therapeutically effective amount of at least one FGF, optionally in combination with a therapeutically effective amount of at least one CSF and/or heparin, may also be used to enhance the production of stem cells or their progeny, or other hemopoietic cells for treatment of a degenerative disease or treatment that produces side effects that lead to degeneration or dysfunction of a tissue, organ, gland or cell, such as following chemotherapy or radiotherapy for malignant diseases.

Preferably, a therapeutically effective amount of at least one FGF, optionally in combination with a therapeutically effective amount of at least one CSF and/or heparin, is administered at a dose from about 0.01 µg to about 2 mg/kg body weight, or any range or value therein, such as presented above for stimulation of stem cells or their progeny, to protect a patient from infections which may result from the myelosuppressive effects of chemotherapy or from the other causes of myelosuppression known the art, as presented herein and as known in the art.

To enhance the engraftment and/or production of bone marrow cells in tissue, glands organ or bone marrow transplantation in donors or recipientss and thereby to promote reconstitution of such tissues gland, organ or bone marrow in a patient undergoing a tissue, organ, gland or bone marrow donation, transplant or engraftment, a therapeutically effective amount of at least one FGFs optionally in combination with a therapeutically effective amount of at least one CSF and/or heparin, is administered up to, during or after the patient's donation or receiving the tissue, gland, organ or bone marrow, which administration to a recipient significantly shortens the "window" prior to the establishment of the graft.

In administration methods of the present invention, a therapeutically effective amount of at least one FGF, optionally in combination with a therapeutically effective amount of at least one CSF and/or heparin, is preferably administered up to one week such as 10, 8, 7, 6, 5, 4, 3, 2 or 1 weeks, prior to the patient's donation, transplant or engraftment.

As used herein, the term "colony stimulating factor" (CSF) is directed to any CSF related cytokines, or lymphokines known in the art which stimulate one or more aspects of hemopoiesis or stem cell development. Such factors include, but are not limited to, stem cell factor, GM-CSF, G-CSF, M-CSF, IL-3, IL-4, and IL-6. See, e.g. , Nienhuis, *New Eng. J. Med.*, 318:916–918 (1988); Brandt et al. (supra) , Cosman, *Immunol. Today* 9:98–98 (1988); and Dorshkind (supra).

The methods of the present invention contemplate the use of at least one CSF and/or heparin, such as 1, 2, 3, 4, 5, 6, 7, 8, 9 or 10 heparins and/or CSFs, or any range therein, in combination with at least one FGF. One of ordinary skill in the art can readily determine which CSF and/or heparin or combination of CSFs and heparins to use, depending on the particular effect or effects desired, as described herein.

According to the present invention, a tissue, gland, organ, bone marrow or peripheral blood stem cell donor is given a therapeutically effective amount of at least one FGF, optionally in combination with a therapeutically effective amount of at least one CSF and/or heparin, preferably from about 0.01 µg/kg body weight up to about 2 mg/kg body weight, such as 0.02, 0.05, 0.07, 0.09, 0.1, 0.5, 1, 3, 5, 7, 9, 10, 20, 50, 70, 90 µg/kg or 0.1, 0.2, 0.5, 0.7, 0.9, 1, 1.5 or 2 mg/kg, or any range or value therein. This treatment is preferably initiated at a time prior to obtaining the tissue, gland, organ, bone marrow or peripheral blood stem cells sufficient for the stem cell number in the tissue, gland, organ, bone marrow or peripheral blood to increase significantly or a measurable amount.

A preferable time of treatment is for a period up to 2 weeks prior to obtaining the tissue, organ, gland, bone marrow or peripheral blood cells. By providing at least one of (i) enhancing engrafting sites in the tissue, organ, gland, bone marrow or peripheral blood cells of a recipient; (ii) enhancing production of stem cells in the donor's tissue, organ, gland, bone marrow or peripheral blood cells; or (iii) increasing the rate of engrafting into the recipient's tissue, organ, gland, bone marrow or peripheral blood cells. In such a way, FGF treatment is designed to enhance the efficiency of grafting donor stem cells or their progeny into a subject to be treated.

In certain instances, autologous or allogenic stem cells or their progeny may be cultured in the presence of a therapeutically effective amount of at least one FGF, optionally in combination with a therapeutically effective amount of at least one CSF and/or heparin, to provide stromal cell "feeder" layers for subsequent generations of primitive stem (stem) cells to be used for implantation into the patient. Known method steps for culture of stromal cells are described, e.g., in Dexter et al., *Long-Term Bone Marrow Culture*, ed. Wright et al., Liss, New York, p. 57–96 (1984) and Dorshkind. et al. *J. Immunol. Meth.* 89:37–47 (1986), which are hereby incorporated entirely by reference.

A therapeutically effective amount of at least one FGF, optionally in combination with a therapeutically effective amount of at least one CSF and/or heparin, may be added to stromal cell cultures to stimulate proliferation of cultured stem cells, stromal cells, or their progeny.

Alternatively, a therapeutically effective amount of at least one FGF, optionally in combination with a therapeutically effective amount of at least one CSF and/or heparin, may be added directly to a tissue, organ, gland, bone marrow or peripheral blood cell culture to increase the numbers of stem cells in a population to be used for transplantation.

The preferred animal subject of the present invention is a mammal. By the term "mammal" is meant an individual belonging to the class Mammalia. The invention is particularly useful in the treatment of human subjects, although it is intended for veterinary uses as well for livestock and domesticated animals.

In addition to bFGF, in the present invention the term "FGF" or "fibroblast growth factor" is intended to encompass other fibroblast growth factors, and functional derivatives thereof, having similar bioactivity for all the uses described herein. Also intended to be included in the term "FGF", "FGFs" or "fibroblast growth factors" are all active forms of FGF derived from the FGF transcript, all muteins with FGF activity and all molecules which may interact with the FGF receptors. Other FGFs known in the art include, e.g., acidic FGF, the hst/K-fgf gene product, FGF-5, int-2 (see Rifkin et al., supra).

Also intended within the scope of the present invention are the alternate molecular forms of FGFs that have FGF biological activity, such as, but not limited to, bFGF, such as those having molecular weights of 17.8, 22.5, 23.1, and 24.2 kDa as determined using known methods of sodium dodecyl sulfate polyacrylamide gel electrophoresis (SDS PAGE). The 17.8 kDa bFGF protein is translationally initiated at the previously predicted methionine (AUG) codon, whereas, the 22.5-, 23.1-, and 24.2-kDa proteins initiate at unusual non-AUG codons. The higher molecular weight forms are collinear N-terminal extensions of the 18 kDa bFGF (Florkiewicz et al., *Proc. Nat'l. Acad. Sci. USA* 86:3978–3981 (1989), which reference is hereby incorporated by reference).

As alternatives to recombinant or purified intact FGF, functional derivatives of the FGF molecule may be used. See, for example, Arakawa et al., European Patent Publication EP320148, which describes recombinant bFGF analogs possessing part or all of the primary structural conformations and the biological properties of human bFGF. In these analogs, at least one of the cysteine residues of the naturally occurring basic fibroblast growth factor is replaced with a different amino acid residue.

Another form of bFGF which can be used according to the present invention is disclosed in Senoo et al. (European Patent Publication EP281822, entirely incorporated by reference herein). The disclosed mutein includes modified, microbiologically-produced bioactive proteins which have the same activities as the naturally-occurring compound but are not capable of forming intermolecular bridges and intramolecular linkages via cysteine residues or others residues which result in the formation of undesirable tertiary structure (e.g., conformations which lower the protein activity).

Alternatively, an FGF used in accordance with the present invention also may include amino acid sequence variants of an FGF polypeptide that can be prepared by mutations in the DNA which encodes the synthesized peptide. Such variants include, for example, deletions from, or insertions or substitutions of, residues within the amino acid sequence. Any combination of deletion, insertion, and substitution may also be made to arrive at the final construct, provided that the final construct possesses the desired activity. Obviously, the mutations that will be made in the DNA encoding the variant peptide must not alter the reading frame and preferably will not create complementary regions that could produce secondary mRNA structure (see, e.g., European Patent Publication No. EP 75,444 entirely incorporated by reference herein).

At the genetic level, prepared by site-directed mutagenesis (as exemplified by Adelman et al., *DNA* 2:183 (1983)) of nucleotides in the DNA or RNA encoding the peptide molecule, thereby producing DNA or RNA encoding the variant, and thereafter expressing the DNA or RNA in recombinant cell culture. The variants typically exhibit the same qualitative biological activity as the nonvariant peptide.

Additionally, modified amino acids or chemical derivatives of amino acids of consensus or fragments, of an FGF according to the present invention, may be provided, which polypeptides contain additional chemical moieties or modified amino acids not normally a part of the protein. Covalent modifications of the peptide are thus included within the scope of the present invention. Such modifications may be introduced into an FGF by reacting targeted amino acid residues of the polypeptide with an organic derivatizing agent that is capable of reacting with selected side chains or terminal residues.

Aromatic amino acids may be replaced with D- or L-naphylalanine, D- or L-Phenylglycine, D- or L-2-thieneylalanine, D- or L-1-, 2-, 3- or 4-pyreneylalanine, D- or L-3-thieneylalanine, D- or L-(2-pyridinyl)-alanine, D- or L-(3-pyridinyl)-alanine, D- or L-(2-pyrazinyl)-alanine, D- or L-(4-isopropyl)-phenylglycine, D-(trifluoromethyl)-phenylglycine, D-(trifluoromethyl)-phenylalanine, D-p-fluorophenylalanine, D- or L-p-biphenylphenylalanine, D- or L-p-methoxybiphenylphenylalanine, D- or L-2-indole(alkyl)alanines, where alkyl may be substituted or unsubstituted methyl, ethyl, propyl, hexyl, buryl, pentyl, non-acidic amino acids, of C1–C20.

Acidic amino acids can be substituted with non-acidic amino acids, and derivatives or analogs thereof, such as the non-limiting examples of (phosphono)-alanine, glycine, leucine, isoleucine, threonine, or serine; or sulfated (e.g., $-SO_3H$) threonine, serine, tyrosine.

Other substitutions may include unnatural hydroxylated amino acids may made by combining "alkyl" (as defined and exemplified herein) with any natural amino acid. Basic amino acids may be substituted with alkyl groups at any position of the naturally occurring amino acids lysine, arginine, ornithine, citrulline, or (guanidino)-acetic acid, or other (guanidino)alkyl-acetic acids, where "alkyl" is define as above. Nitrile derivatives (e.g., containing the CN-moiety in place of COOH) may also be substituted for asparagine or glutamine, and methionine sulfoxide may be substituted for methionine.

In addition, any amide linkage in any of an FGF may be replaced by a ketomethylene moiety, e.g. (—C(=O)—CH$_2$—) for (—(C=O)—NH—). Such derivatives are expected to have the property of increased stability to degradation by enzymes, and therefore possess advantages for the formulation of compounds which may have increased in vivo half lives, as administered by oral, intravenous, intramuscular, intraperitoneal, topical, rectal, intraocular, or other routes.

In addition, any amino acid of the said peptides can be replaced by the amino acid of the opposite chirality. Thus, any amino acid naturally occurring in the L-configuration (which may also be referred to as the R or S, depending upon the structure of the chemical entity) may be replaced with an amino acid of the same chemical structural type, but of the opposite chirality, generally referred to as the D- amino acid but which can additionally be referred to as the R- or the S-, depending upon its composition and chemical configuration. Such derivatives have the property of increased stability to degradation by enzymes, and therefore are advantageous in the formulation of compounds which may have longer in vivo half lives, when administered by oral, intravenous, intramuscular, intraperitoneal, topical, rectal, intraocular, or other routes.

Additional amino acid modifications of amino acids of an FGF of the present invention may include the following:

Cysteinyl residues may be reacted with alpha-haloacetates (and corresponding amines), such as 2-chloroacetic acid or chloroacetamide, to give carboxymethyl or carboxyamidomethyl derivatives. Cysteinyl residues may also be derivatized by reaction with compounds such as bromotrifluoroacetone, alpha-bromo-beta-(5-oimidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues may be derivatized by reaction with compounds such as diethylprocarbonate e.g., at pH 5.5–7.0 because this agent is relatively specific for the histidyl side chain, and para-bromophenacyl bromide may also be used; e.g., where the reaction is preferably performed in 0.1M sodium cacodylate at pH 6.0.

Lysinyl and amino terminal residues may be reacted with compounds such as succinic or other carboxylic acid anhydrides. Derivatization with these agents is expected to have the effect of reversing the charge of the lysinyl residues. Other suitable reagents for derivatizing alpha-amino-containing residues include compounds such as imidoesters/ e.g., as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate.

Arginyl residues may be modified by reaction with one or several conventional reagents, among them phenylglyoxal, 2,3-butanedione, 1,2-cyclohexanedione, and ninhydrin according to known method steps. Derivatization of arginine residues requires that the reaction be performed in alkaline conditions because of the high pKa of the guanidine functional group. Furthermore, these reagents may react with the groups of lysine as well as the arginine epsilon-amino group.

The specific modification of tyrosyl residues per se is well-known, such as for introducing spectral labels into tyrosyl residues by reaction with aromatic diazonium compounds or tetranitromethane. N-acetylimidizol and tetranitromethane may be used to form O-acetyl tyrosyl species and 3-nitro derivatives, respectively.

Carboxyl side groups (aspartyl or glutamyl) may be selectively modified by reaction with carbodiimides (R'—N—C—N—R') such as 1-cyclohexyl-3-(2-morpholinyl-(4-ethyl)carbodiimide or 1-ethyl-3-(4-azonia-4,4-dimethylpentyl)carbodiimide. Furthermore, aspartyl and glutamyl residues may be converted to asparaginyl and glutaminyl residues by reaction with ammonium ions.

Glutaminyl and asparaginyl residues may be frequently deamidated to the corresponding glutamyl and aspartyl residues. Alternatively, these residues may be deamidated under mildly acidic conditions. Either form of these residues falls within the scope of the present invention.

Derivatization with bifunctional agents is useful for cross-linking the peptide to a water-insoluble support matrix or to other macromolecular carriers, according to known method steps. Commonly used cross-linking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-[(p-azidophenyl)dithio]propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 (which are herein incorporated entirely by reference), may be employed for protein immobilization.

Other modifications of an FGF used in a method of the present invention may include hydroxylation of proline and lysine, phosphorylation of hydroxyl groups of seryl or threonyl residues, methylation of the alpha-amino groups of lysine, arginine, and histidine side chains (T. E. Creighton, *Proteins: Structure and Molecule Properties*, W. H. Freeman & Co., San Francisco, pp. 79–86 (1983)), acetylation of the N-terminal amine, and, in some instances, amidation of the C-terminal carboxyl groups, according to known method steps.

Such derivatized moieties may improve the solubility, absorption, biological half life, and the like. Such moieties or modifications of an FGF may alternatively eliminate or attenuate any undesirable side effect of the protein and the like. Moieties capable of mediating such effects are disclosed, for example, in *Remington's Pharmaceutical Sciences*, 16th ed., Mack Publishing Co., Easton, Pa. (1980).

Such chemical derivatives of an FGF also may provide attachment to solid supports, such as for purification, generation of antibodies or cloning; or to provide altered physical properties, such as resistance to enzymatic degradation or increased binding affinity or modulation for an FGF, which is desired for therapeutic compositions comprising an FGF, antibodies thereto or fragments thereof. Such peptide derivatives are known in the art, as well as method steps for making such derivatives.

Having now generally described the invention, the same will be more readily understood through reference to the following example which is provided by way of illustration, and is not intended to be limiting of the present invention.

EXAMPLE 1

LONG TERM CULTURE OF HUMAN BONE MARROW STROMAL CELLS IN THE PRESENCE OF AN FGF

The effect of an FGF on human bone marrow stromal cells, using bFGF as an exemplary FGF, was examined as a means for circumventing the difficulty of obtaining sufficient numbers of such cells.

A. MATERIALS AND METHODS

Recombinant human bFGF was obtained from Synergen Inc. (Boulder, Colo.). Trypsin, heparin, and hydrocortisone were obtained from Sigma Chemical Co. (St. Louis, Mo.). The alpha minimal essential medium (αMEM) was obtained from Flow Laboratories (McLean, Va.). Fetal calf serum was obtained from Armour Pharmaceutical CO (Kankakee, Ill.), and horse serum, from GIBColo. (Grand Island, N.Y.).

Human bone marrow stromal cells were obtained from healthy adult volunteers who had given informed consent. Buffy coat cells were seeded at a concentration of $3\times10^6$/ml in "stromal medium" which consisted of αMEM containing 12.5% fetal calf serum, 12.5% horse serum, $10^{-6}$M hydrocortisone, $10^{-4}$M 2-mercaptoethanol, 1.6 mM glutamine and antibiotics. A layer of adherent cells was obtained within 2-3 weeks. Nonadherent cells were removed by extensive washing, and the adherent cell layer was passaged by first treating with 0.25% trypsin containing 0.02% EDTA to dislodge the cells. bFGF was added at the indicated concentrations. Fresh "stromal medium" was added at 48 hr intervals when testing the effects of bFGF on the growth of bone marrow stromal cells.

B. RESULTS

1. Morphology

Figure 1C:
Figure 1D:
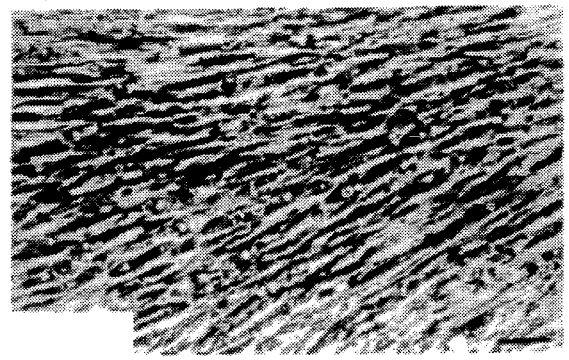

The effects of bFGF on the morphology of bone marrow stromal cells in culture were striking, as shown in FIG. 1a–1d. The elongated fibroblastic morphology of stromal cells was altered by bFGF so that cells had a more compact morphology (FIGS. 1a and 1b). bFGF also altered the appearance of confluent cultures of cells. In the presence of bFGF, the cells grow to high density in multilayers, while their counterparts, maintained in the absence of bFGF, were contact inhibited at a low cell density (FIGS. 1c and 1d).

2. Growth

The addition of bFGF increased the density of the primary stromal cell layer. Primary marrow buffy coat cells were seeded in "stromal medium" at $3\times10^6$ cells/ml per 35 mm dish in the presence of 0, 0.2, 2, or 20 ng/ml bFGF and the cell number on duplicate dishes was determined 15 days later. As shown in Table 1, a 5-fold increase in cell density was noted when cells were cultured in the presence of 20 ng/ml bFGF; 0.2 ng bFGF/ml approximately doubled the cell density.

TABLE 1

The Effect of bFGF on the Growth of Primary Bone Marrow Stromal Cells

| bFGF (ng/ml) | Cells/dish × $10^4$ |
| --- | --- |
| 0 | 33.1 |
| 0.2 | 64.0 |
| 2. | 107.5 |
| 20 | 156.5 |

Primary bone marrow buffy coat cells were seeded in stromal medium at $3\times10^6$ cells per 35 mm petri dish in the absence or presence of the indicated concentrations of bFGF. Cell numbers were determined on duplicate dishes after 15 days.

Culturing stromal cells continuously in the presence of bFGF delayed their senescence considerably. Stromal cells had a limited proliferative potential and senesced after approximately 2 generations, whereas cells cultured continuously in the presence of bFGF survived to approximately 26 generations, as shown in Table 2.

TABLE 2

Effect on bFGF on the Senescence of Bone Marrow Stromal Cells

| | Cell Generation | |
| --- | --- | --- |
| Experiment | Control | bFGF Treated |
| 1 | ND[a] | 29 |
| 2 | 3.1 | 21.8 |
| 3 | 0.8 | 16.8 |
| 4 | 1.4 | 39.5 |
| 5 | 1.8 | 24.7 |
| 6 | 2.2 | ND |

Bone marrow was removed from 6 healthy volunteers and cultured in the absence and continuous presence of 20 ng/ml bFGF. At 10–13 day intervals the monolayers were removed with trypsin and $1.3 \times 10^6$ cells were added to 75 cm² flasks. This process was continued until cell growth ceased.
[a]Not determined.

Figure 2:
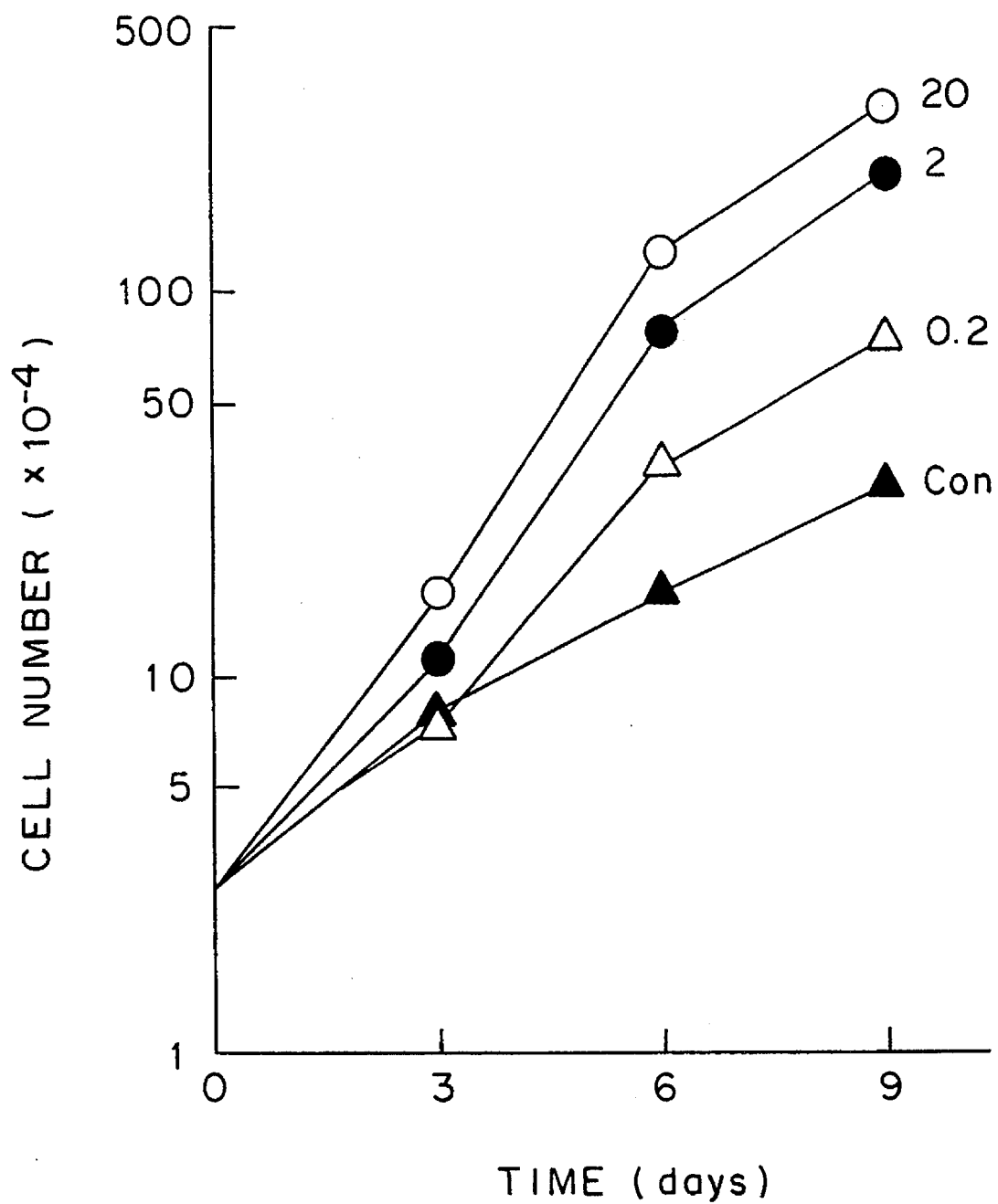
FIG. 2 is a graph showing the effect of various concentrations of bFGF on bone marrow stromal cell growth. Bone marrow stromal cells that had been passaged 3 times were seeded in stromal medium at $3 \times 10^4$ cells per 35 mm culture dish in the absence (▲) or presence of bFGF at 20 (o), 2(●), or 0.2 (Δ) ng/ml bFGF. Duplicate dishes were removed and the cell numbers determined at the indicated times.

Stimulatory effects on growth were also noted when stromal cell layers that had been passaged in culture were subsequently exposed to bFGF. FIG. 2 illustrates the effect of varying concentrations of bFGF on stromal cells that had been passaged 3 times prior to its addition. Dishes treated with 20 ng/ml bFGF for 9 days contained 10 times the number of cells as found in untreated cultures. Low concentrations of bFGF (0.2 ng/ml) also significantly enhanced cell growth.

Figure 3:
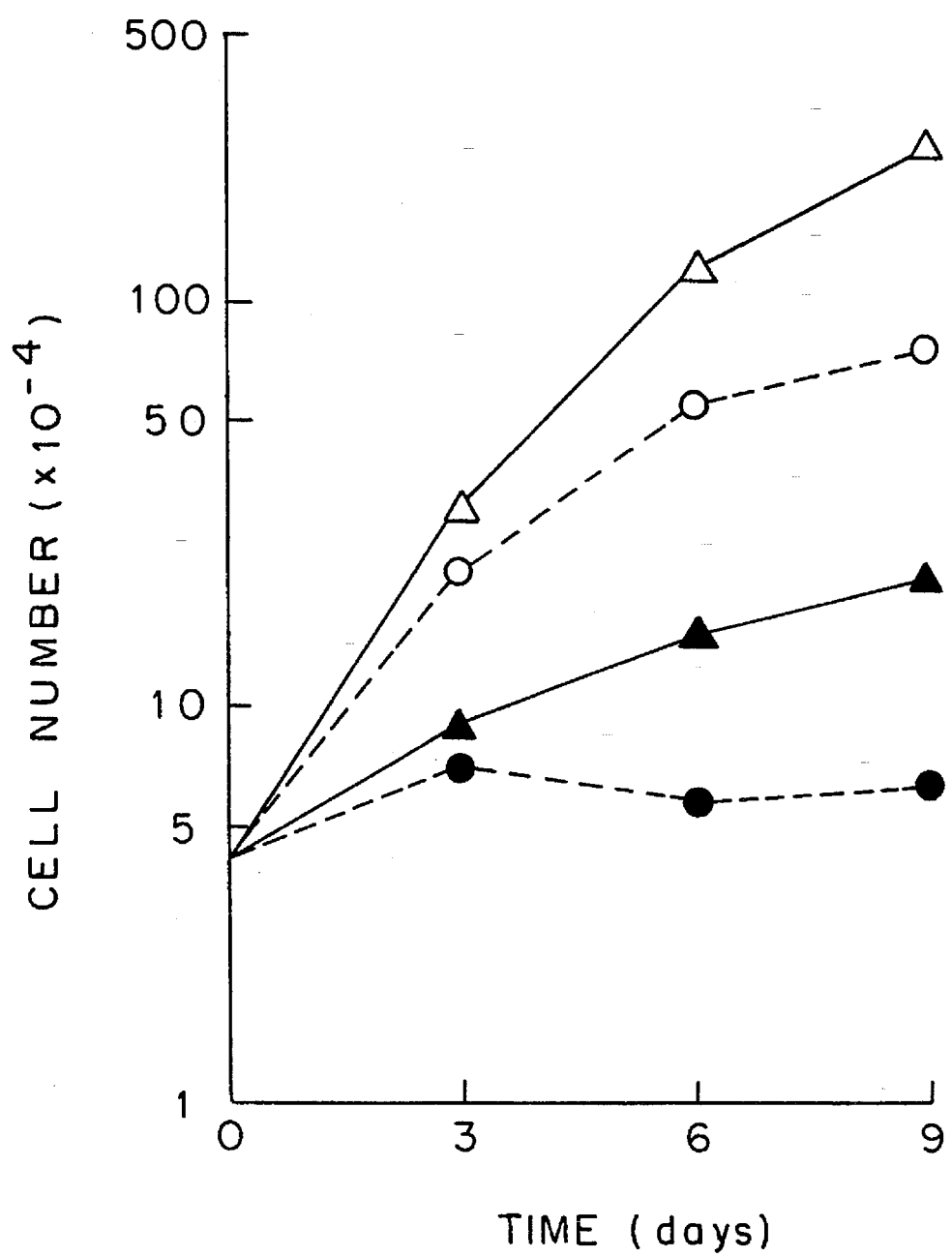
FIG. 3 is a graph showing the effect of bFGF on growth of bone marrow stromal cells in different media. Bone marrow stromal cells that had been passaged twice were seeded at $6 \times 10^4$ cells per 35 mm dish in stromal medium (▲—▲), stromal medium containing 20 ng/ml bFGF (Δ—Δ), RPMI-1640 (with 10% FCS) (●—●) or RPMI-1640 (with 10% FCS)+20 ng/ml bFGF (o—o). Duplicate dishes were removed and cell numbers were determined at the indicated times.

Stromal cells had a very limited proliferative potential when cultured in RPMI-1640 medium supplemented with 10% fetal calf serum, as shown in FIG. 3. The addition of bFGF at 20 ng/ml to this medium greatly increased the proliferative potential of stromal cells; for example after 9 days of culture, with bFGF, a 12-fold increase in cell number was noted. Cells cultured in the presence of 20 ng/ml bFGF grow at a faster rate than those in "stromal medium" without bFGF. However, cells cultured in RPMI-1640+bFGF did not reach as high a final density as cells cultured in "stromal medium"+bFGF.

Figure 4:
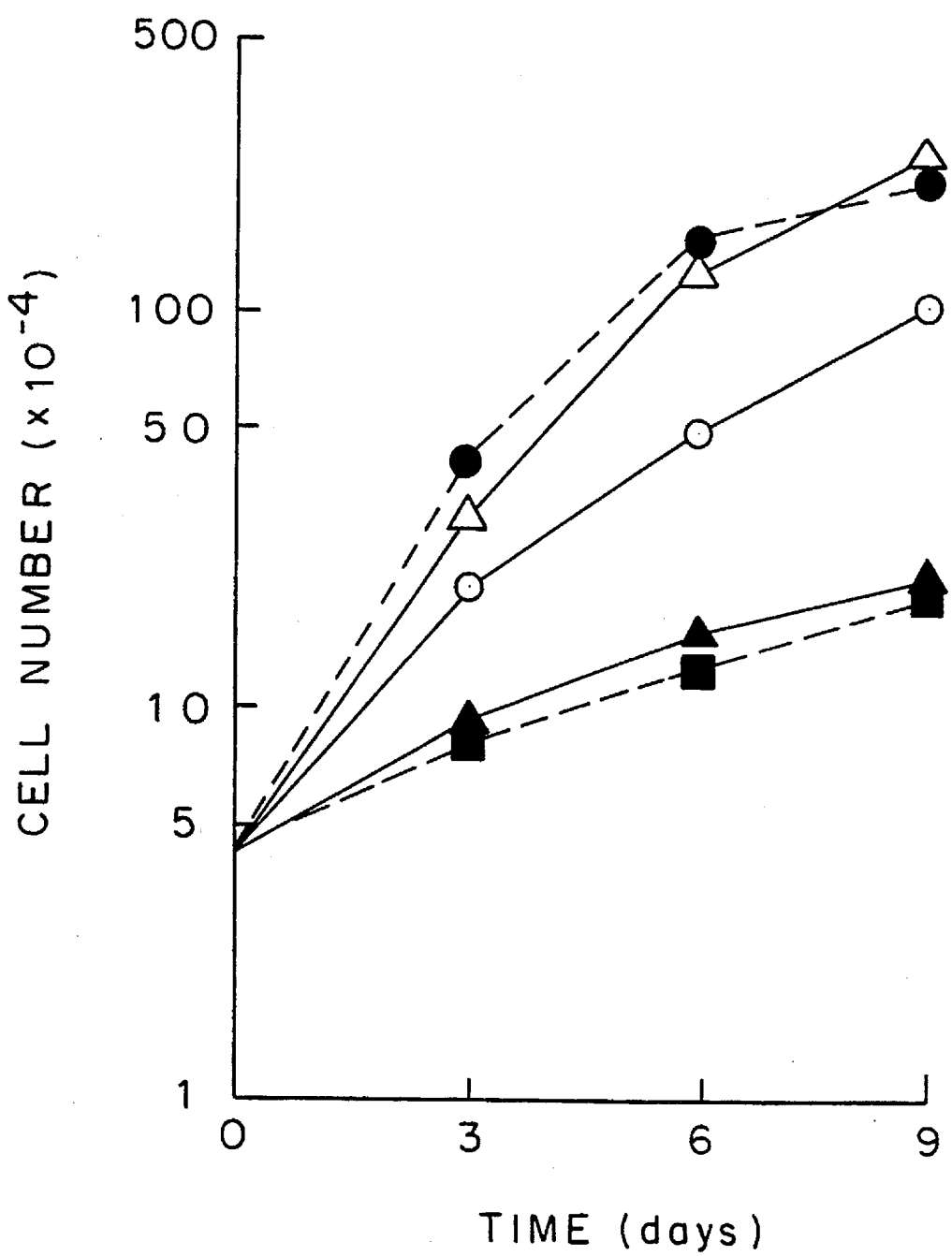
FIG. 4 is a graph showing the potentiation of the effects of bFGF on stromal cell growth by heparin. Bone marrow stromal cells that had been passaged twice were seeded at $6 \times 10^4$ cells per 35 mm dish in stromal medium alone (▲—▲); stromal medium containing: 2 ng/ml bFGF (o—o); 20 ng/ml bFGF (Δ—Δ); 2 ng/ml bFGF and 20 µg/ml heparin (●—●); and 20 µg/ml heparin alone (■—■). Duplicate dishes were removed and the cell numbers were determined at the indicated times.

Heparin potentiated the growth stimulation by bFGF. The growth rate of cells cultured in the presence of 2 ng/ml bFGF and 20 µg/ml heparin was substantially greater than the growth rate of cells cultured in the presence of bFGF alone, and was somewhat greater than the growth rate of cells cultured in the presence of 20 ng/ml bFGF, as shown in FIG. 4. Heparin alone, at 20 µg/ml, had little effect on cell growth.

Figure 5:
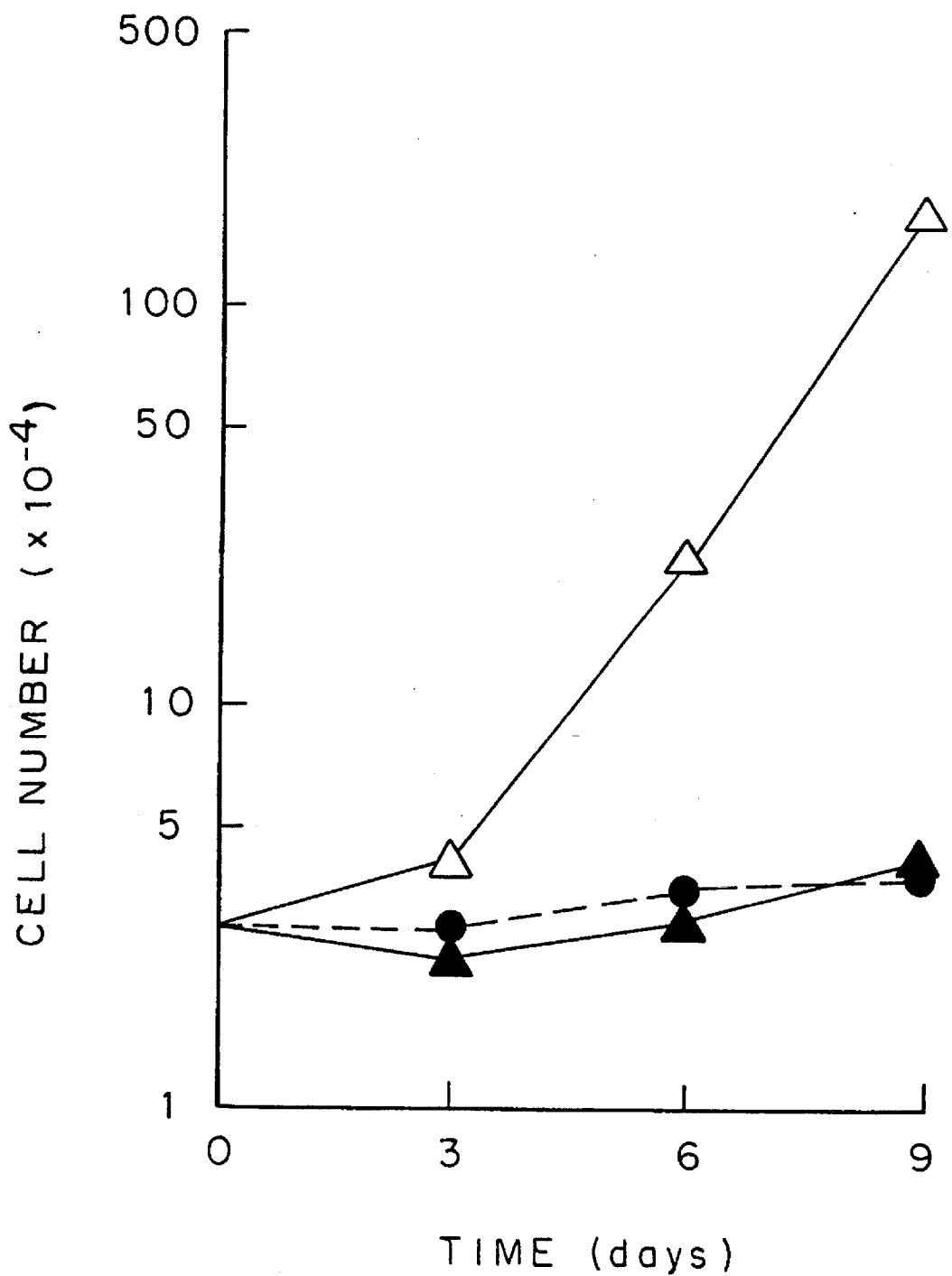
FIG. 5 is a graph showing the reversibility of the effects of bFGF on cell growth. Bone marrow stromal cells that had been passaged 4 times were used. bFGF at 20 ng/ml was added to some cultures which were passaged twice in the presence of bFGF over a period of 5 weeks. These cultures were then trypsinized and seeded at $3 \times 10^4$ cells per 35 mm dish either in the continued presence of 20 ng/ml bFGF (Δ—Δ) or following its removal prior to trypsinization (●—●). Companion cultures that had been passaged 4 times without bFGF were seeded at the same density (▲—▲). Duplicate dishes were removed, and the cell numbers were determined at the indicated times.

The effects of bFGF on stromal cell growth were fully reversible. Cells that were cultured in the presence of 20 ng/ml bFGF for 2 passages over 5 weeks had the same rate of growth as untreated cells if the bFGF was removed prior to trypsinization and passaging of the monolayer, as shown in FIG. 5. In contrast, significant stimulatory effects on growth were noted when bFGF was added to stromal cells for brief periods of time.

Figure 6:
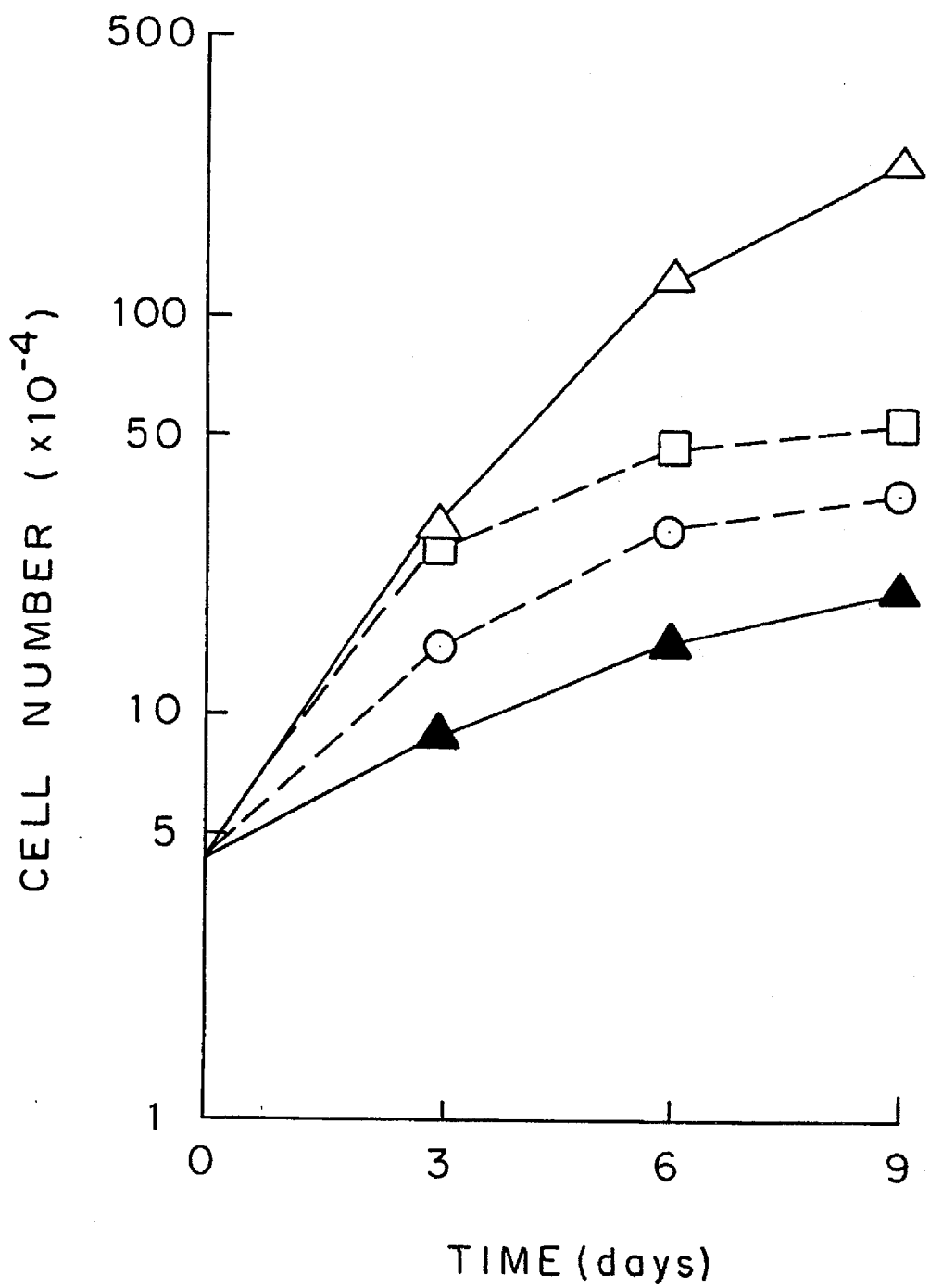
FIG. 6 is a graph showing the effects of brief exposure to bFGF on bone marrow stromal cell growth. Bone marrow stromal cells that had been passaged twice were seeded at $6 \times 10^4$ cells per 35 mm dish. Medium alone (▲—▲) or medium containing 20 ng/ml bFGF was added to sets of culture dishes for 4 hr (o—o), 24 hr (□—□), or continuously (Δ—Δ). Following removal of bFGF-containing medium, the cultures were washed 3 times with 2 ml of stromal medium, and stromal medium alone was then added to these dishes. Duplicate dishes were removed and cell numbers were determined at the indicated times.

Even a brief exposure to bFGF stimulates cell growth (FIG. 6). A 3-fold increase in cell number was noted when the bFGF was added to cells for 24 hours before being removed and replaced with regular stromal medium.

Figure 7:
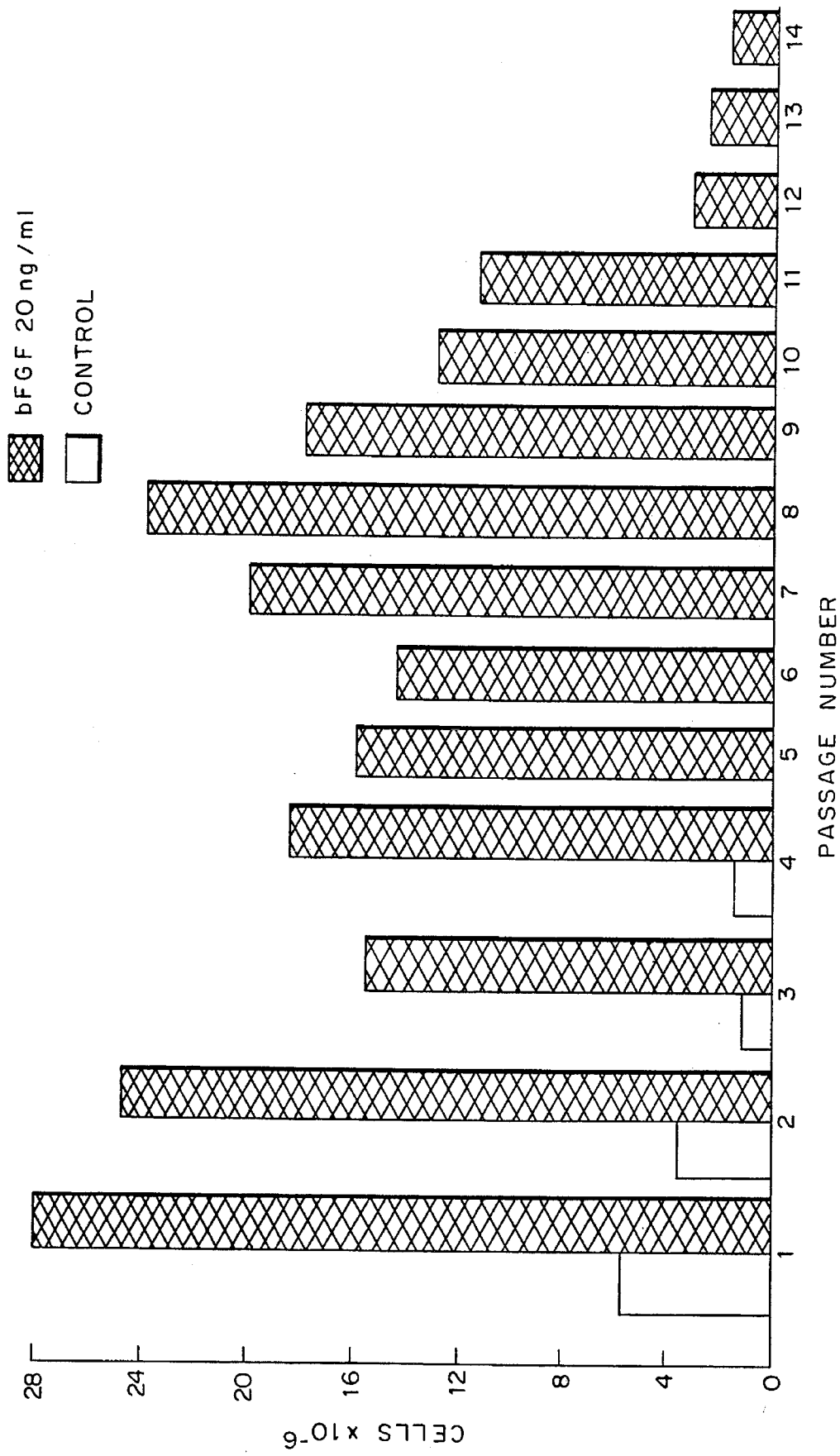
FIG. 7 is a bar graph comparing the density of cells cultured in the presence of bFGF versus control cells. Bone marrow stromal cells were seeded at $2\times10^7$ buffy coat cells/75 cm$^2$ flask in the absence and presence of 20 ng/ml bFGF. At 10–12 day intervals, the cell number on each set of flasks was determined, and the cells were passaged at $1.3\times10^6$/75 cm$^2$ flask.

Cells cultured in the presence of bFGF reached a much higher density than cells in control medium (FIG. 7). Also, cells cultured in the presence of bFGF could be passaged many more times before senescence occurred. This occurred after approximately 26 generations, as compared to about 2 generations for cells cultured without bFGF. As exemplified by bFGF, FGFs can therefore be used to generate large numbers of human bone marrow stromal cells, which has not previously been possible.

Figure 8:
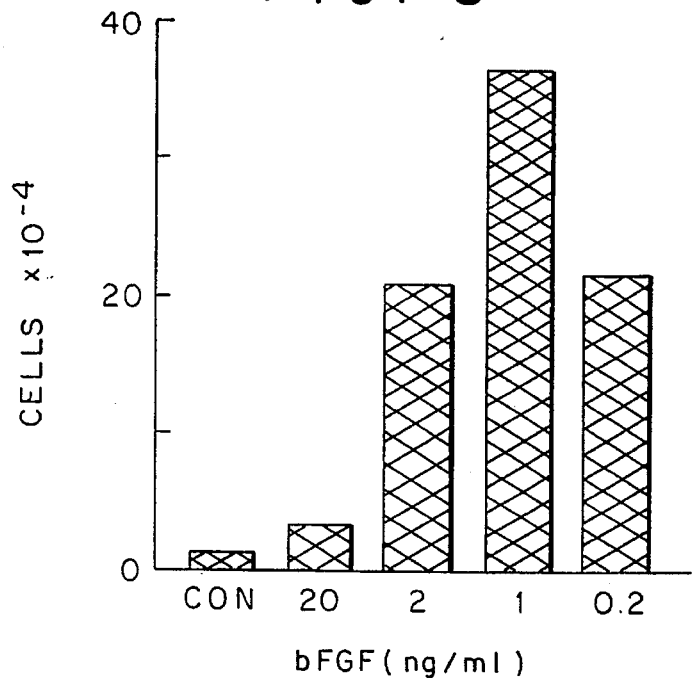
FIG. 8 is a bar graph showing enhancement in the generation of hemopoietic progenitors by bFGF. Human bone marrow cells were seeded at $2\times10^7$ buffy coat cells/75 cm$^2$ flask in the absence and presence of 20, 2, 1, and 0.2 ng/ml bFGF. An adherent stromal cell layer containing foci of hemopoietic stem cells was established. The number of cells released into the culture medium was determined.

It should be noted that bFGF increased the number of hemopoietic cells released into the culture medium (FIG. 8). FGFs, as exemplified by basic FGF, therefore, under these conditions, significantly stimulate the generation of hemopoietic stem cells in conjunction with a stromal cell layer in situ or in vitro.

Figure 9:
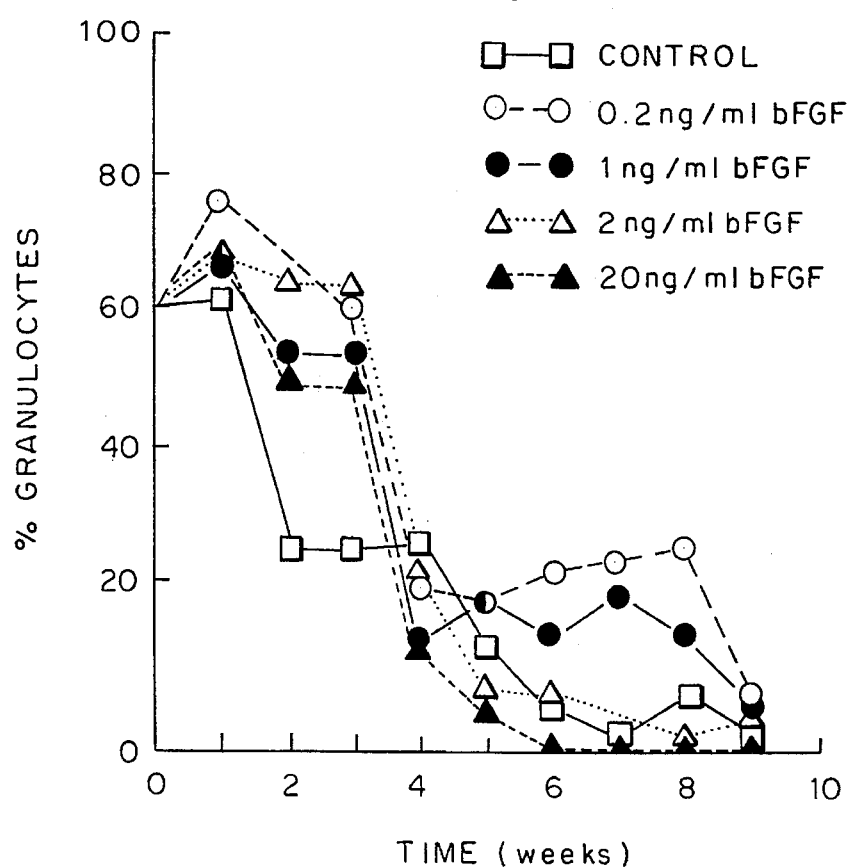
FIG. 9 is a graph showing release of granulocytes into culture medium under the influence of bFGF. Human bone marrow was seeded at $2\times10^7$ buffy coat cells/75 cm$^2$ flask in the absence and presence of 20, 2, 1, and 0.2 ng/ml bFGF. At various intervals, cells in the supernatant were harvested and slides were prepared. A differential cell count identified the percentage of different cell types present in the specimens.
Figure 11:
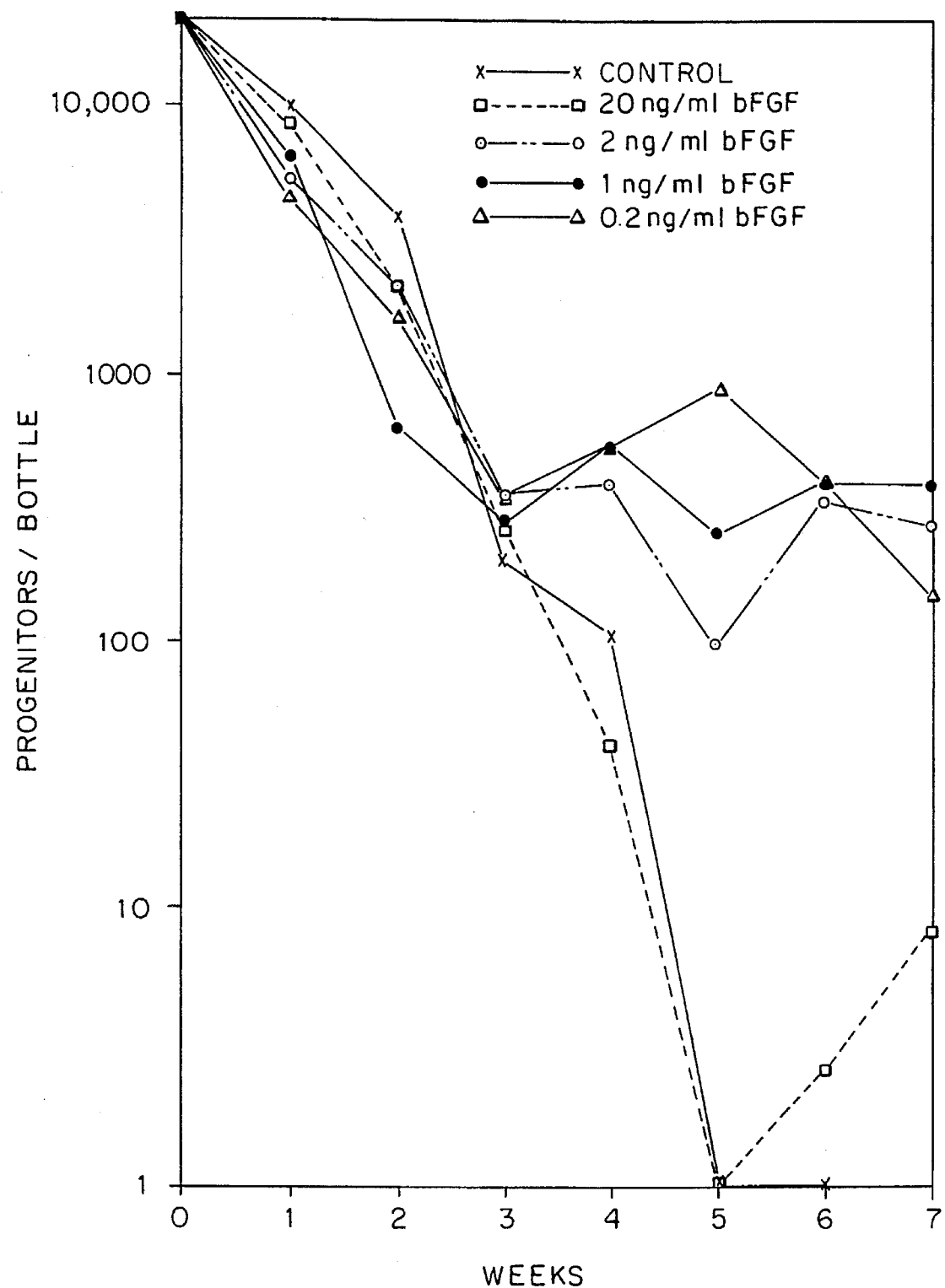
FIG. 11 is a graph illustrating that low concentrations of bFGF increase the stem cell population in the medium. Human bone marrow was seeded at $2\times10^7$ buffy coat cells/75 cm$^2$ flask in the absence and presence of 20, 2, 1 and 0.2 ng/ml bFGF. At weekly intervals cells in the supernatant were harvested and seeded in soft agar in the presence of GM-CSF and colonies were counted after 14 days. Similar results were obtained after 7 days of culture and with G-CSF or 5637-CM.

The addition of low concentrations of bFGF to cell cultures resulted in an increased percentage of granulocytes shed into the medium (FIG. 9). This experiment demonstrates that FGFs, as exemplified by bFGF are expected to enhance the production of cells of the myeloid lineage. The enhanced production by treatment with at least one FGF, according to the present invention, of granulocytes following bone marrow transplantation or following chemotherapy for malignant disease is therefore expected to protect patients against infections as a general immune system stimulant.

bFGF at all concentrations tested stimulated the generation of stem cells able to respond to CSFs in vitro (FIGS. 10a–10c and 11). GM-CSF, G-CSF, and 5637-conditioned medium (CM) all stimulated the growth of myeloid progenitors. GM-CSF acts on more primitive stem cells than G-CSF, and 5637-CM contains a mixture of different cytokines. The progenitors present in the medium of cells cultured with bFGF were therefore of myeloid origin.

Figure 12:
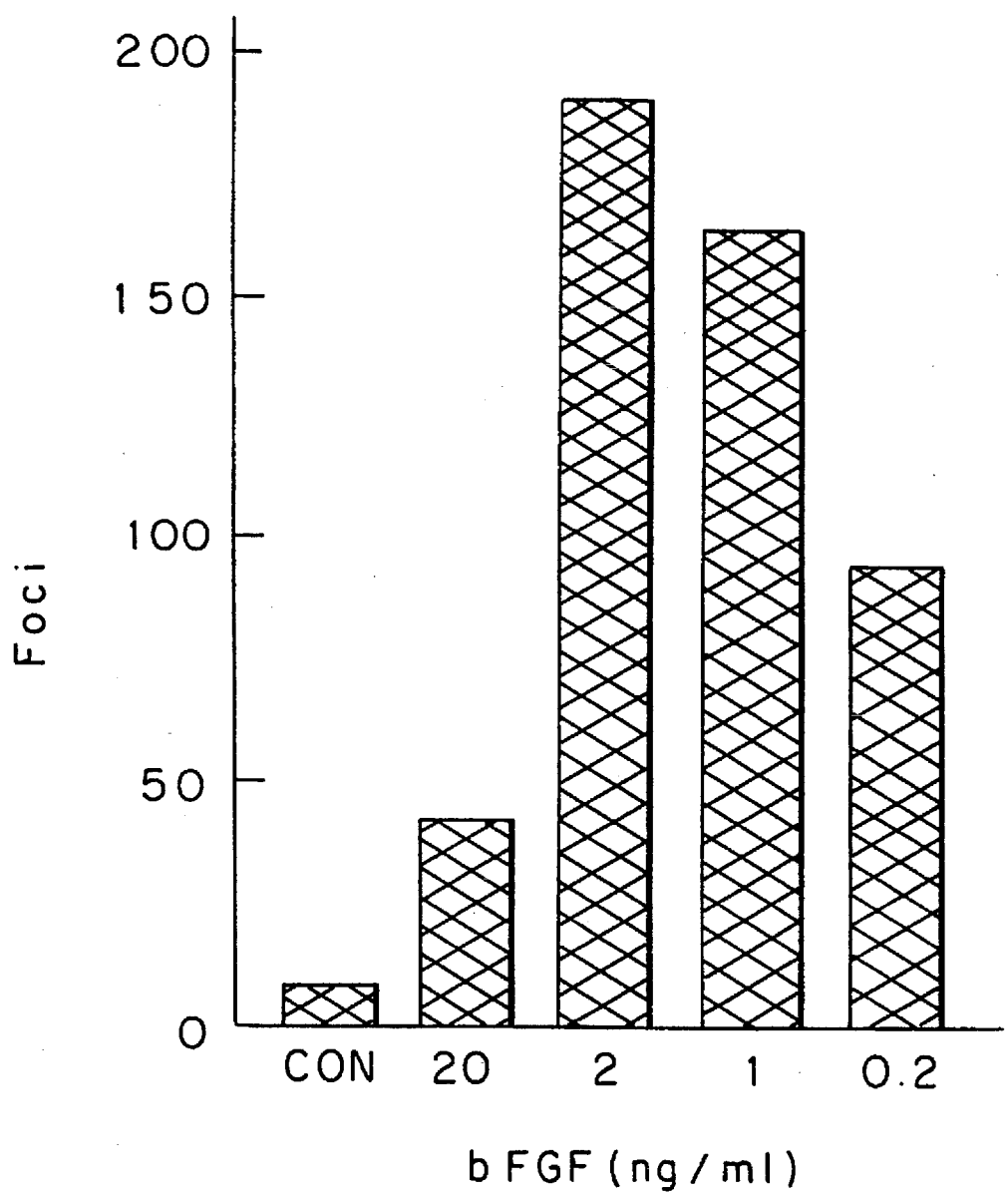
FIG. 12 is a bar graph showing establishment of an adherent stromal cell layer containing foci of hemopoietic stem cells in the presence of bFGF. Human bone marrow cells were seeded at $2\times10^7$ buffy coat cells/75 cm$^2$ flask in the absence and presence of 20, 2, 1, and 0.2 ng/ml bFGF. An adherent stromal cell layer containing foci of hemopoietic stem cells was established.

The presence of bFGF in culture increased the number of cobblestone stem cell-containing foci in the stromal cell layer (FIG. 12). As shown by bFGF, FGFs are expected to promote the development of foci of stem cells in the adherent stromal layer and enhanced hemopoiesis in conjunction with the stromal cell layer, according to methods of the present invention.

C. DISCUSSION

Basic FGF has previously been shown to be a potent mitogen for many mesoderm-derived cells and to delay senescence in certain cultured cells (Gospodarowicz et al., In Vitro 14:85–118 (1978); Gospodarowicz et al., In Ford and Maizel (eds), *Mediators in Cell Growth and Differentiation*, Raven Press, New York, 1985, pp 109–13; Gospodarowicz et al., *Endocr. Rev.* 8:95–114 (1987)).

The present inventors have shown that at concentrations, as low as 0.2 ng/ml, FGFs, as shown by bFGF, is a potent mitogen for bone marrow stromal cells, as well as for enhancing the final density attained by bone marrow stromal cell cultures, resulting in the stromal cells having formed dense multilayered sheets and having a transformed morphology. These effects are fully reversible using bFGF and are expected to be reversible for FGFs generally. After exposure to an FGF for prolonged periods of time, once the FGF is removed from the medium and the cells are trypsinized and passaged, the cell growth rate is expected to revert to one comparable to that of untreated cells as demonstrable by bFGF.

It has been demonstrated that bFGF binds to heparin sulfates present in cell matrices, and that interaction with heparin and heparin sulfate protects bFGF from proteolytic degradation (Sommer et al., *J. Cell. Physiol.* 138:215–220 (1989); Saksela et al., *J. Cell Biol.* 107:743–751 (1988)). Matrix binding of FGFs is expected to provide a reservoir of growth factor and may provide a continuous source of ligand for the specific high affinity receptors on the surfaces of cells (Moscatelli *J. Cell Biol.* 107:753–759 (1988); Flaumenhaft et al., i J. Cell. Physiol. 140:75–81 (1989)). It has been shown herein that significant stimulation of growth follows a transient (4 hour) exposure of stromal cells to bFGF. Heparin potentiates the growth stimulating effect of bFGF, which may be because heparin protects bFGF from proteolytic degradation.

Bone marrow stromal cells are an important component of the hemopoietic system and are known to be a source of the colony stimulating factors necessary for growth and differentiation of hemopoietic stem cells. Basic FGF has been produced and isolated from preparations of bovine bone matrix (Hauschka et al., *J. Biol. Chem.* 261:12665–12674 (1986)), and FGFs are expected to be a important factors required for the function and proliferation of the stromal cell component of a hemopoietic system in vitro, in vivo or in situ.

As shown by an FGF, when added to stromal medium, any FGF stimulates hemopoiesis as the stimulation of growth and/or hemopoiesis in vivo, in vitro, and in situ, e.g., as presented in Table 3, wherein $2 \times 10^7$ bone marrow cells were inoculated and cultured as presented in the present Example.

TABLE 3

| bFGF (ng/ml) | Stromal Cells/Flask | Progenitors/Flask |
| --- | --- | --- |
| 0 | $4.0 \times 10^6$ | $299 \pm 106$ |
| 0.2 | $6.6 \times 10^6$ | $1920 \pm 240$ |
| 1.0 | $9.8 \times 10^6$ | $5713 \pm 1187$ |
| 2.0 | $8.3 \times 10^6$ | $4309 \pm 456$ |
| 20.0 | $9.2 \times 10^6$ | $2296 \pm 420$ |

Additionally, the use of a therapeutically effective amount of at least one FGF, optionally in combination with a therapeutically effective amount of at least one CSF and/or heparin, allows the growth of large numbers of human hemopoietic bone marrow stem cells and/or stromal cells in vivo, in vitro, and in situ, as a more readily available source of hemapoiesis for use in bone marrow transplantation, engraftment and culturing, as well as for the treatment of immune suppression in immunosuppressive diseases and as the result of chemotherapy.

EXAMPLE 2

STIMULATION OF MYELOID PROGENITOR CELLS, EVEN OVER THE SUPPRESSIVE EFFECT OF TGF-β bFGF is found to at least partially negate the suppressive effects of TGF-β1 on GM-CSF supported progenitor cell growth in that it significantly augments GM-CSF but not granulocyte colony stimulating factor (G-CSF) mediated progenitor cell development.

Materials and Methods

Reagents

Recombinant human GM-CSF and recombinant human G-CSF were obtained from Amgen (Thousand Oaks, Calif.): both colony stimulating factors had a specific activity of $1 \times 10$ units/mg protein in a standard bone marrow CFU-GM assay. Recombinant human TGF-beta 1 was obtained from Genentech (South San Francisco, Calif.). Stock solutions were stored at 4° C. Recombinant human bFGF was obtained from Synergen (Boulder, Colo.). Stock vials were stored at −20° C. For each experiment, all factors were diluted in serum containing medium on the day of use. Neutralizing antibody to TGF-beta 1 was obtained from R & D Systems (Minneapolis, Minn.) and stored at −20° C. Dilutions of this antibody were performed on the day of use. Rabbit IgG was used as a source of irrelevant antibody. An FITC conjugated anti-CD34 antibody, HPCA-1, was purchased from Becton Dickinson (San Jose, Calif.). Human gamma globulin was obtained from Miles Inc./Cutter Biological (Elkart, Ind.).

Cell Separation Techniques

Bone marrow cells were obtained from healthy volunteers after informed consent. The mononuclear cells were isolated by centrifugation on Ficoll-Hypaque gradients (1.077 g/cm, Pharmacia Fine Chemicals, Piscataway, N.J.), washed twice in phosphate buffered saline (PBS) and suspended in Iscove's modified Dulbecco's medium (IMDM) containing 10% fetal calf serum (FCS) (Hyclone, Logan, Utah) supplemented with penicillin (100 U/ml) (GIBCO, Grand Island, N.Y.), streptomycin (100 µg/ml) (GIBCO) and 3 mg/ml glutamine (GIBCO). These cells were used as target cell populations for the CFU-GM progenitor cell assay.

CD34 enriched cell populations were prepared as follows. Mononuclear cells were washed twice in PBS and resuspended in IMDM. Subsequently, cells (50×10 cells per plate) were allowed to adhere to plastic tissue culture plates (Corning, Corning N.Y.), for 90 minutes. Non-adherent cells were removed, washed twice, resuspended at 15×10 cells/4 ml in PBS containing of 0.1% human gamma globulin and incubated for 15 minutes at room temperature. Four milliliter suspensions were then transferred to AIS MicroCELLector T-25 flasks coated with soybean agglutinin (Applied Immune Sciences, Menlo Park, Calif.), to remove soybean agglutinin positive cells as previously described (Lebkowski J. S., Schain L. R., Okrongly D., Levinsky R., Harvey M., Okarma T. B. Rapid isolation of human CD34 hematopoietic stem cells: purging of human tumor cells. Transplantation (in press) September–October, 1992).

After one hour of incubation on a non-vibrating surface, supernatant cells were removed. Flasks were then washed three times to remove any residual non-adherent cells. The nonadherent cell population was then washed twice in PBS, resuspended at 15×10/4 ml in PBS containing 0.1% human gamma globulin and incubated for 15 minutes at room temperature. Cell suspensions were subsequently transferred to AIS MicrCELLector T-25 flasks coated with anti-CD34 antibodies (Applied Immune Sciences, Menlo Park, Calif.).

Nonadherent cells were removed after 1 hour incubation at room temperature on a nonvibrating surface. Flasks were washed three times to remove any residual nonadherent cells. Ten milliliters of PBS containing 10% FCS was then added to each flask and adherent cells removed by manual agitation of the flasks. The final cell population was found to be 70–97% positive for CD34, as analyzed by flow cytometry utilizing an FITC conjugated anti-CD34 antibody, HPCA-1. Morphologically, these cells were greater than 90% blasts.

CFU-GM

Low density or CD34+ cells were cultured in 35 mm tissue culture dishes (Corning, Corning N.J.) at 10 or 5×10 cells/ml McCoy's modified assay medium, respectively, containing 0.3% agar (Difco, Detroit Mich.) and 10% FCS, as previously described (Gabrilove et al., *Blood* 66:407, 1985). Cultures were stimulated by the addition of either 1, 2, 10 or 20 ng/ml of GM-CSF or 100 ng/ml G-CSF alone or in combination with bFGF at 1, 10, 100 or 1000 ng/ml. For inhibition experiments, TGF-beta 1, at concentrations of 1, 5 and 10 ng/ml, was added to cultures alone or in the presence of GM-CSF, G-CSF, bFGF or combinations thereof. Dishes were incubated at 37° C. in a 2 humidified atmosphere flushed with 5% CO in air. Cultures were scored with an inverted microscope after 7 and 14 days and the number of clusters (<40 cells) and colonies (>40 cells) determined.

Statistical Analysis

Statistical analyses were performed by a generalization of the paired t test that utilizes information regarding between plate as well as inter-experimental variation (Rosner, *Applied Statistics* 31:9–13, 1982). Comparison of progenitor cell growth under different conditions was performed by logarithmic transformation of the raw data in order to normalize the data distribution.

Results

Figure 13B:
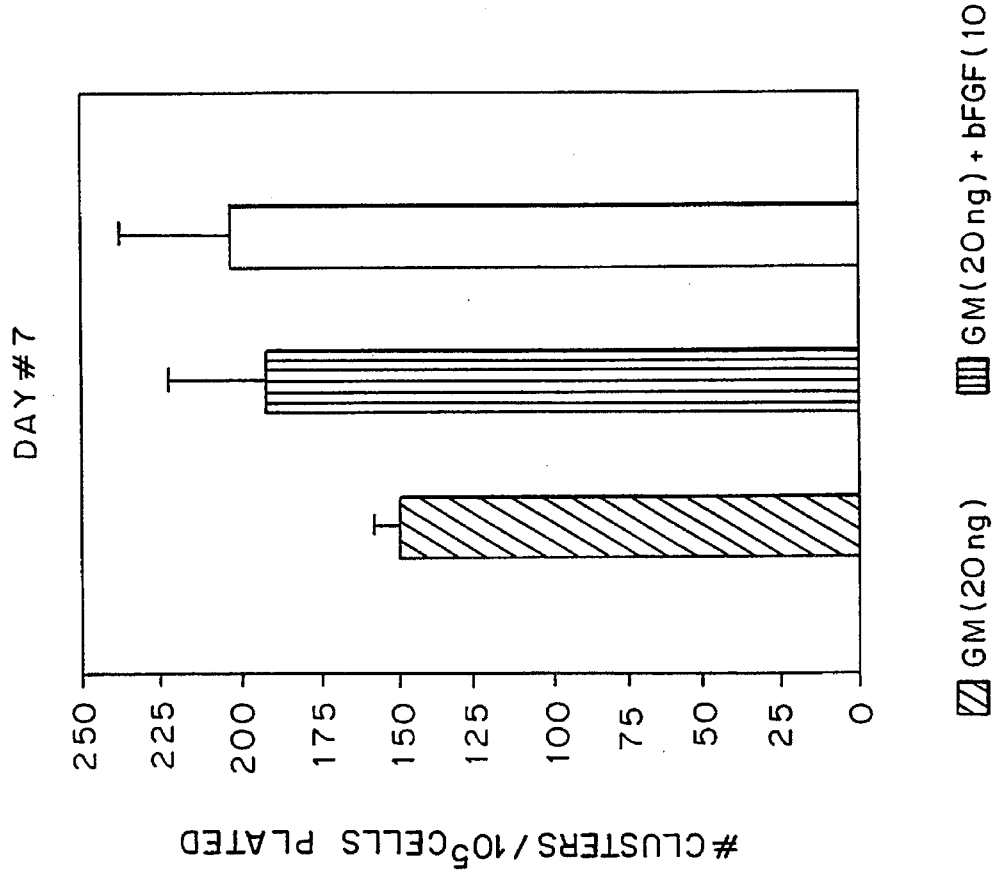
FIG. 13A–B. bFGF induced augmentation of GM-CSF mediated day 7 cluster 2 (FIG. 13A) and day 14 colony (FIG. 13B) formation. $10^5$ Low density human bone marrow cells/dish were cultured in 0.3% agar in the presence of 20 ng/ml GM-CSF alone or in combination with 100, 10 or 1 ng/ml of bFGF. No growth was observed with bFGF alone. The data represent the mean ±1 SD of three replicate plates scored in one experiment.
Figure 13A:
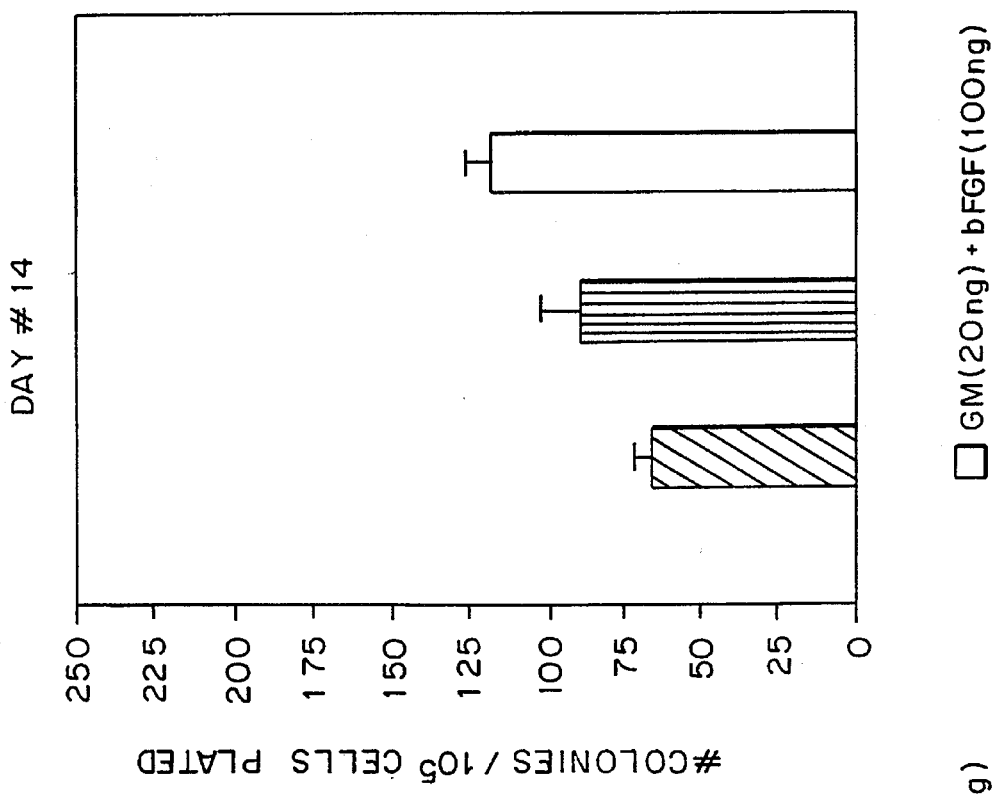

Augmentation of GM-CSF stimulated progenitor cell growth by bFGF. The ability of bFGF to augment progenitor cell growth from human bone marrow alone or in combination with G-CSF or GM-CSF was investigated in semisolid agar cultures. Low density bone marrow cells were stimulated with either 20 ng/ml of GM-CSF or 100 ng/ml of G-CSF, in the presence or absence of 1, 10 or 100 ng/ml of bFGF. Plates were scored after 7 and 14 days of culture. No CFU-GM growth was observed in the presence of 1, 10 or 100 ng/ml of bFGF alone. When cells were cultured in the presence of 20 ng/ml of GM-CSF in combination with either 10 or 100 ng/ml of bFGF, a significant augmentation in day 7 cluster (FIG. 13A) and day 14 colony (FIG. 13B) growth was observed as compared to cells cultured in the presence of the same concentration of GM-CSF alone. In this experiment, a 30% increase and 35% increase in day 7 cluster formation were observed when cells stimulated with GM-CSF were costimulated with 10 and 100 ng/ml of bFGF respectively (p<0.05: FIG. 13A). This augmentation of GM-CSF supported day 7 cluster formation was consistently observed in eight other experiments and ranged from 30–100%. When the data from nine experiments were pooled this augmentation was found to be statistically significant (p=0.0001). 100 ng/ml of bFGF was as effective as 1000 ng/ml of bFGF in augmenting GM-CSF mediated growth.

Partial abrogation of TGF-beta 1 mediated suppression by bFGF

The degree of variability observed in the augmentation of GM-CSF mediated progenitor cell growth by bFGF could reflect differences in negative regulators, such as TGF-beta, found either in fetal calf serum or produced endogenously by various cell populations from different donor marrows. In particular, TGF-beta was found to be present in FCS and in conditioned medium obtained from 24 hour suspension cultures of low density bone marrow cells. For this reason, the contribution of TGF-beta 1 present in progenitor cell cultures on the growth of GM-CSF supported CFU-GM was investigated. This was done by incorporating neutralizing antibodies to TGF-beta 1 in the semisolid agar cultures at the time that cells were seeded. In the absence of GM-CSF, no increase in spontaneous cluster or colony formation was noted in the presence of 1, 5 or 10 µg/ml of neutralizing antibody to TGF-beta 1 or relevant IgG; however, the addition of 1, 5 or 10 µg/ml or anti-TGF-beta 1 antibody to agar cultures stimulated by GM-CSF resulted in a 40–100% augmentation in day 7 cluster formation (Table 3). A definite augmentation was always observed when GM-CSF cultures were co-incubated with at least 5 µg/ml of anti-TGF-beta 1 IgG (Table 3). No effect on progenitor cell growth was observed when GM-CSF supported cultures were incubated with irrelevant IgG (Table 3). Neutralizing antibody added to CD34 enriched cells failed to augment GM-CSF mediated progenitor cell growth suggesting that the FCS did not contribute significantly to biologically active TGF-beta 1. This observation is further supported by other investigators (Massague, *Ann. Rev. Cell Biol.* 6: 597–641, 1990), who have previously reported that the TGF-beta 1 present in serum is biologically inactive. Therefore, it appears that endogenous TGF-beta 1 production decreases the number of GM-CSF dependent clusters and colonies suggesting that clonogenic growth reflects the balance of endogenously produced positive and negative regulators elaborated within the culture during incubation.

Based on these data and the published observations that 1) TGF-beta 1 inhibits GM-CSF mediated progenitor cell growth (Ishibashi et al., *Blood* 69:1737, 1987; Ohta et al., *Nature* 329:539, 1987; Sing et al., *Blood* 72:1504, 1988; Sing et al., *J Cell Biochem.* 39:107, 1989), and 2) bFGF counteracts the inhibitory effects of TGF-beta on endothelial cells (Fefeur et al., *Growth Factors* 3:237, 1990), bFGF is expected to, and found to, counteract the inhibitory effect of TGF-beta 1 on progenitor growth.

Figure 14A:
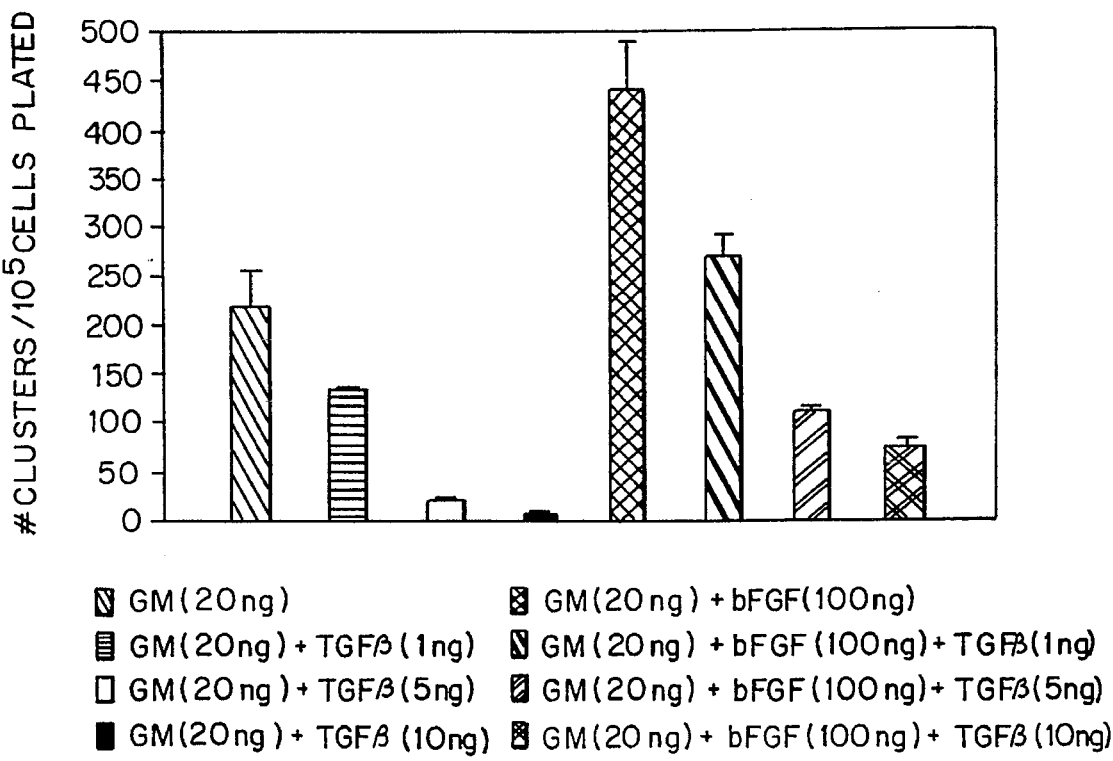
FIG. 14A–B. Partial abrogation of TGF-beta 1 mediated suppression of GM-CSF stimulated progenitor cell growth by bFGF. $10^5$ low density human bone marrow cells/dish were cultured in 0.3% agar in the presence of GM-CSF alone, GM-CSF plus TGF-beta 1, GM-CSF plus bFGF or GM-CSF plus bFGF and TGF-beta 1. No growth was observed with bFGF or TGF-beta 1 alone. The data represent the mean ±1 SD of three replicate plates scored in one experiment.

For these experiments, low density bone marrow cells were incubated with either 1, 5 or 10 ng/ml of TGF-beta 1; 1, 10 or 100 ng/ml of bFGF; 10 or 20 ng/ml of GM-CSF alone or in combination. The results of one representative study for day 7 cluster formation are depicted in FIG. 14A. In this experiment, 20 ng/ml of GM-CSF stimulated the growth of 219±38 clusters (FIG. 14A). When 10 ng/ml of TGF-beta 1 was concomitantly added to cultures stimulated with the same dose of GM-CSF, only 8±5 clusters or 4% of the original growth observed with GM-CSF alone, was noted (FIG. 14A). Cells stimulated with 20 ng/ml of GM-CSF plus 100 ng/ml of bFGF supported the growth of 442±52 clusters, illustrating significant augmentation of GM-CSF induced growth (p<0.001:FIG. 14A). In this instance, the addition of 10 ng/ml of TGF-beta 1 reduced the number of clusters to 74±8 (FIG. 14A). This represented 17% of the original growth observed with bFGF plus GM-CSF. Therefore, a four fold increase in growth was preserved when 100 ng/ml of bFGF was included in GM-CSF cultures exposed to 10 ng/ml of TGF-beta 1 as compared to the growth noted in the absence of bFGF (p<0.01: FIG. 14A). The protective influence of bFGF on TGF-beta 1 mediated suppression of day 7 cluster formation was also noted when 5 ng/ml of TGF-beta 1 was employed. Twenty-five percent of the clusters stimulated by GM-CSF plus bFGF were observed using this concentration of TGF-beta 1 compared to only 9% of the clusters when TGF-beta 1 was added to cultures stimulated by GM-CSF alone (FIG. 14A). When the data from four separate experiments were pooled, the protective effect of bFGF was found to be statistically significant (p=0.0092). Cultures stimulated by GM-CSF or GM-CSF plus bFGF were equally inhibited by low concentrations (1 ng/ml) of TGF-beta 1 resulting in 70% or 62% of the growth observed in the absence of 1 ng/ml of TGF-beta 1 respectively (FIG. 14A).

Figure 14B:
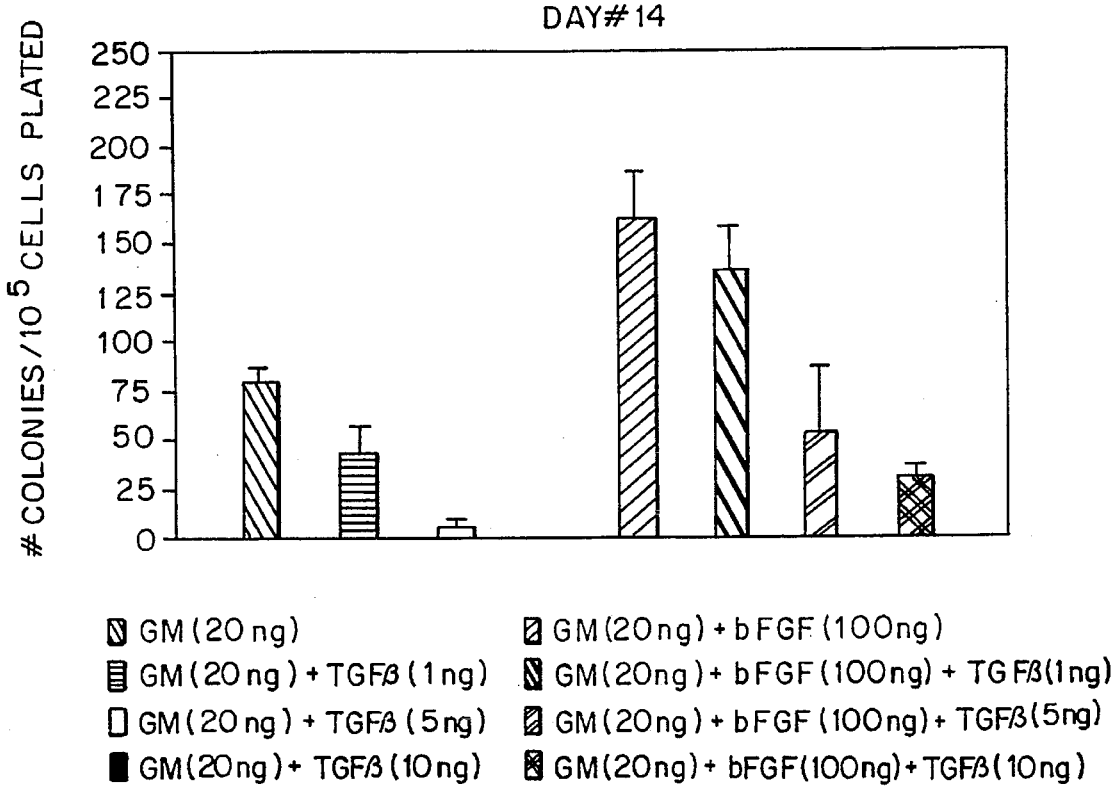

The same pattern of protection by bFGF from TGF-beta 1 mediated inhibition of GM-CSF stimulated progenitor cell growth was observed for day 14 colony formation (FIG. 14B). On day 14, 81±6 colonies were observed with GM-CSF alone (FIG. 14B). The addition of 10 or 5 ng/ml of TGF-beta 1, resulted in either a complete abrogation or only 6% of the growth observed with GM-CSF alone.

In contrast, 162±26 colonies were noted when cells were cultured in the presence of GM-CSF plus 100 ng/ml bFGF (significantly increased over that observed with GM-CSF alone, p<0.001). In this instance, 100 ng/ml of bFGF added to cultures containing GM-CSF plus 10 ng/ml or 5 ng/ml of TGF beta 1 yielded 8% and 30% of the growth respectively (FIG. 14B).

For day 14 colonies, bFGF appeared to be protective even when low concentrations of TGF-beta 1 (1 ng/ml) were used. The addition of 1 ng/ml of TGF-beta 1 to cultures stimulated by GM-CSF plus bFGF resulted in a reduction of only 16% in the observed number of colonies compared to a reduction of 47% in colony growth noted in the absence of bFGF (FIG. 14B).

Figures 15A, 15B:
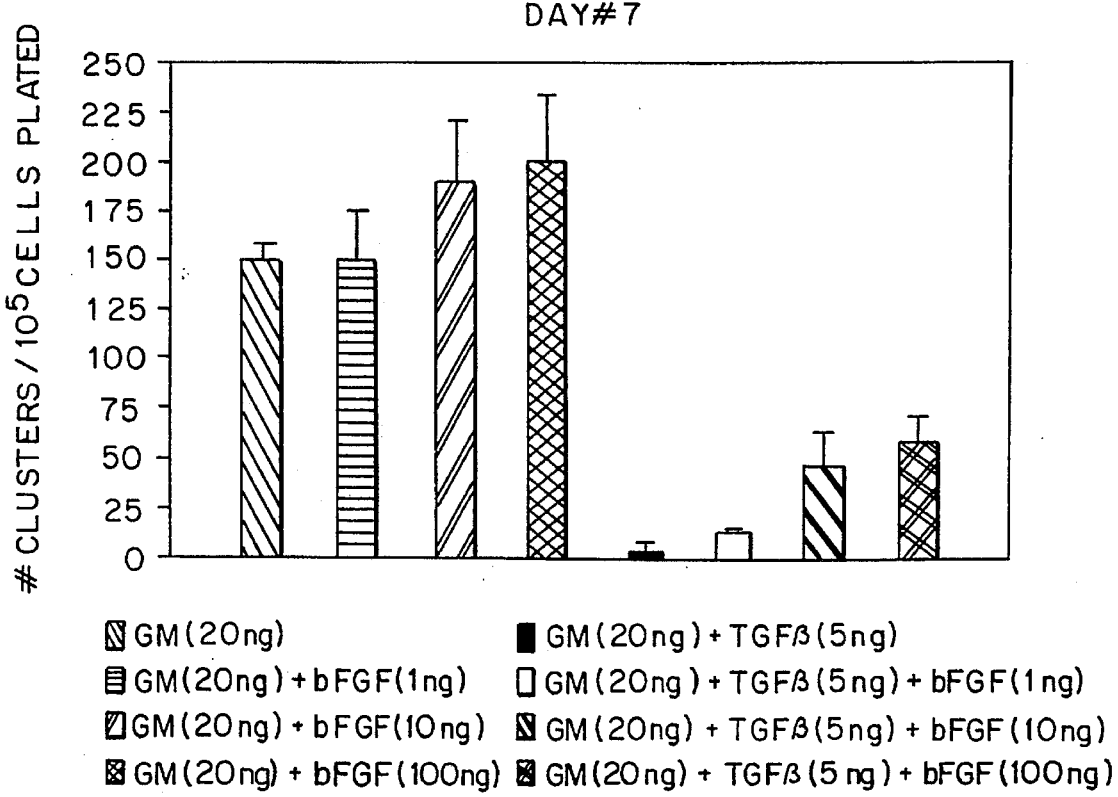
FIG. 15A–B. Basic FGF abrogates TGF-beta 1 mediated suppression of GM-CSF supported progenitor cell growth in a dose dependent manner. $10^5$ low density human bone marrow cells/dish were cultured in the presence or absence of GM-CSF alone, GM-CSF plus bFGF or GM-CSF plus bFGF and TGF-beta 1. The data represent the mean ±1 SD of three replicate plates.

The partial abrogation of TGF-beta 1 mediated suppression of GM-CSF supported progenitor cell growth by bFGF was also found to be dependent on the concentration of bFGF employed (FIG. 15A and 15B). In this experiment GM-CSF stimulated 150±9 clusters on day 7 (FIG. 15A) and 66±5 colonies on day 14 (FIG. 15B). This clonogenic growth was markedly diminished in the presence of 5 ng/ml of TGF-beta 1 resulting in the growth of only 6±3 day 7 clusters (FIG. 15A) and 8±1 day 14 colonies (FIG. 15B). This represented 3 and 11% of the growth observed with GM-CSF alone.

In contrast, 100 ng/ml bFGF plus GM-CSF stimulated 202±35 day 7 clusters (FIG. 15A) and 118±7 day 14 colonies (FIG. 15B). Despite the addition of 5 ng/ml of TGF-beta 1 to cultures stimulated by bFGF plus GM-CSF, 60±13 clusters (FIG. 15A) and 44±14 colonies (FIG. 15B) were still observed on day 7 and 14, respectively. This represented 30% and 67% of the growth obtained in the absence of TGF-beta 1. These results differed markedly from the almost complete abrogation of progenitor cell development by TGF beta 1 in the absence of bFGF. Ten ng/ml of bFGF was also effective in partially abrogating the inhibitory effect of TGF-beta 1 on day 7 cluster formation, allowing for 24% of the original cluster growth to be maintained compared to only 11% when no bFGF was added (FIG. 15A). Ten ng/ml of bFGF, however, was ineffective in reversing the suppressive effect of this dose of TGF-beta 1 on day 14 GM-CSF supported colony formation (FIG. 15B).

The ability of bFGF to partially abrogate the inhibitory effect of TGF-Beta 1 was also noted in three separate experiments when CD34 enriched cells were cultured in a CFU-GM assay. As demonstrated in this representative experiment (Table 4), bFGF significantly abrogated TGF-beta 1 mediated suppression of day 7 (p<0.003) and day 14 (p<0.0004) GM-CSF supported progenitor cell growth.

TABLE 4

Partial abrogation of TGF-beta 1 mediated suppression of progenitor cell growth by bFGF utilizing CD34 enriched bone marrow cells

| GROWTH FACTOR | DAY 7* | DAY 14* |
| --- | --- | --- |
| None | 0 | |
| bFGF 100 ng/ml | 0 | 0 |
| GM-CSF 20 ng/ml | 47 ± 18 | 81 ± 12 |
| GM-CSF 20 ng + TGFB 5 ng | 6 ± 7[1] | 14 ± 5[1] |
| GM-CSF 20 ng + bFGF 100 ng | 59 ± 18 | 84 ± 16 |
| GM-CSF 20 ng + FGF 100 ng + TGFB 5 ng | 26 ± 10 | 25 ± 10 |

*total CFG-GM ± standard deviation of eight individual culture dishes scored (5 × 10³ CD34+ cells/dish)
[1]p <0.003 for day 7 and p <0.0001 for day 14. P values were calculated comparing the difference between the reduction in clonogenic growth observed with GM-CSF 20 ng and GM-CSF 20 ng + TGFB 5 ng as compared to GM-CSF 20 ng + bFGF 100 ng and GM-CSF 20 ng + TGFB 5 ng + bFGF 100 ng bFGF, in a dose dependent fashion, is found to abrogate TGF-beta 1 mediated suppression of GM-CSF supported progenitor cell growth. TGF-beta 1 within the culture dish also is found to decrease the clonogenic response to GM-CSF.

These data along with the observation that an FGF augments GM-CSF mediated progenitor cell growth suggest that FGFs generally are expected to enhance myelopoiesis by modulating the inhibitory response to TGF-beta 1, in vivo, in situ and in vitro.

FGFs are expected to stimulate or diminish the production of positive or negative regulatory cytokines. FGFs are also or alternatively expected to modulate receptor expression for growth factors with either proliferative or inhibitory effects on myelopoiesis.

Finally, FGFs are expected to increase the release of CSFs from cell surfaces and/or matrices and make them available for progenitor stimulation.

FGFs are also expected to partially abrogate the inhibitory action of TGF-beta 1. Significant inhibition of human bone marrow GM-CSF was also shown by supported day 14 colony formation with 5 and 10 ng/ml of TGF-beta 1. In addition, as a marked inhibition of day 7 GM-CSF stimulated cluster formation, a direct action of bFGF on the progenitor cell is expected, and single cell experiments utilizing CD34+Lin− cells will confirm that the effects of bFGF are directly mediated on the progenitor or require the presence of specific accessory cells.

It is also expected that FGFs will modulate TGF-beta 1 receptor expression on progenitor cells and thereby diminish the inhibitory effects of this cytokine. The partial abrogation of the inhibitory effect of TGF-beta by FGFs, is also expected to explain the augmentation of myelopoiesis observed in bFGF stimulated long term bone marrow cultures (Wilson et al *Blood* 77:954, 1991). Eaves et al (*Blood* 78: 110–117, 1991), have previously demonstrated TGF-beta mRNA as well as nanogram levels of TGF-beta bioactivity in conditioned medium from human long term bone marrow cultures. FGFs are expected to counteract this negative regulatory effect in the long term bone marrow culture system.

EXAMPLE III

CULTURED MONONUCLEAR AND CD34+ CELLS HAVING SYNERGISTIC GROWTH EFFECTS IN THE PRESENCE OF FGF AND OTHER STIMULATING GROWTH FACTORS

Mononuclear and CD34+ cells were cultured according to the above Examples.

Figure 16A:
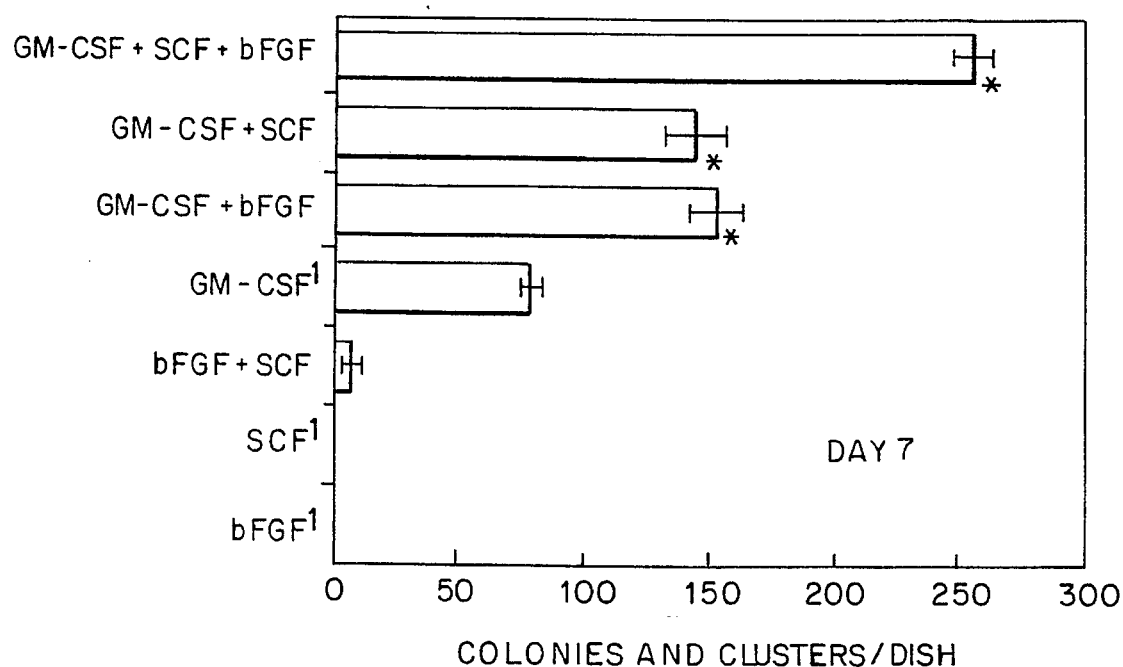
FIG. 16A–B presents a graphical representation of the response of low density bone marrow cells to bFGF, SCF and GM-CSF alone and in combination (16A=7d., 16B=14d.).
Figure 16B:
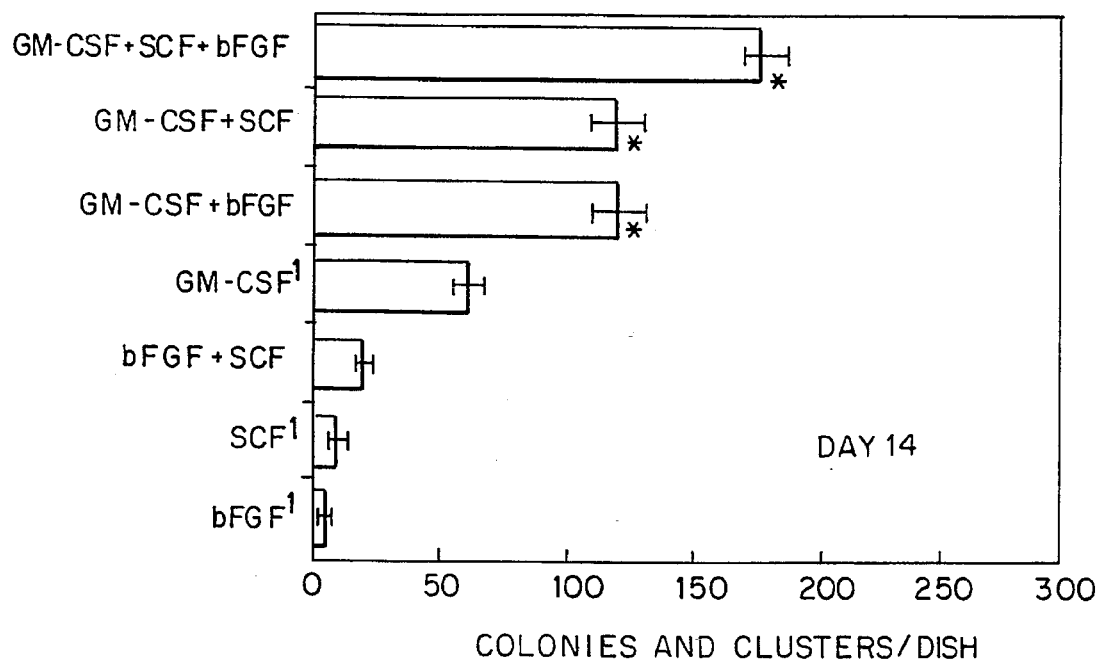
Figure 17A:
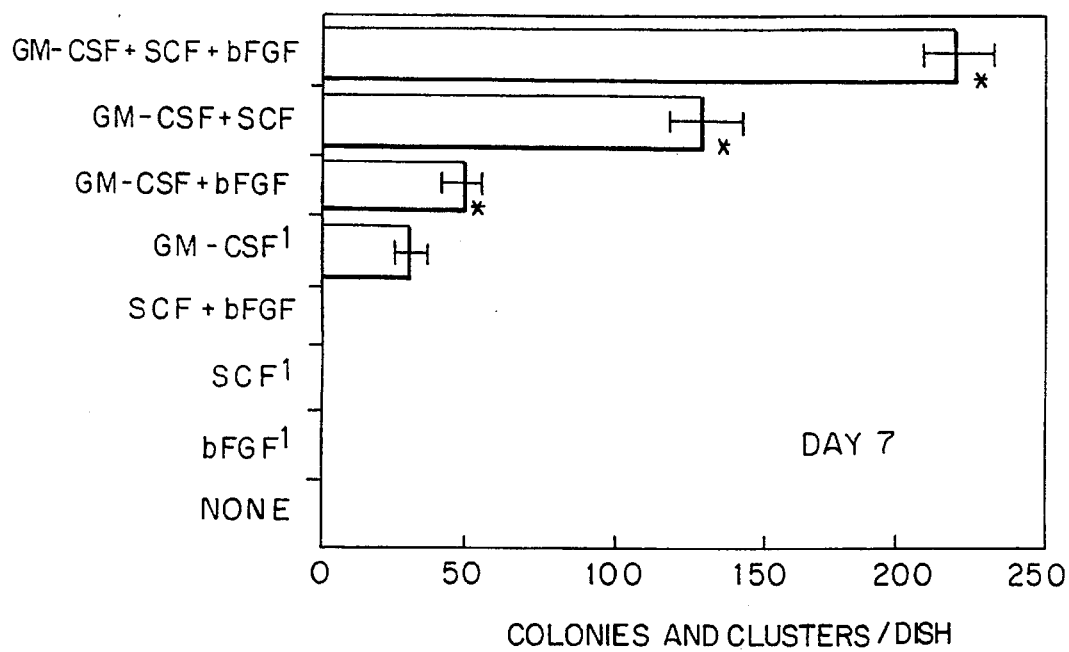
FIG. 17A–B is a graphical representation of the response of CD34$^+$ progenitor cells to bFGF, SCF and GM-CSF alone and in combination (17A=7d., 17B=14d.).
Figure 17B:
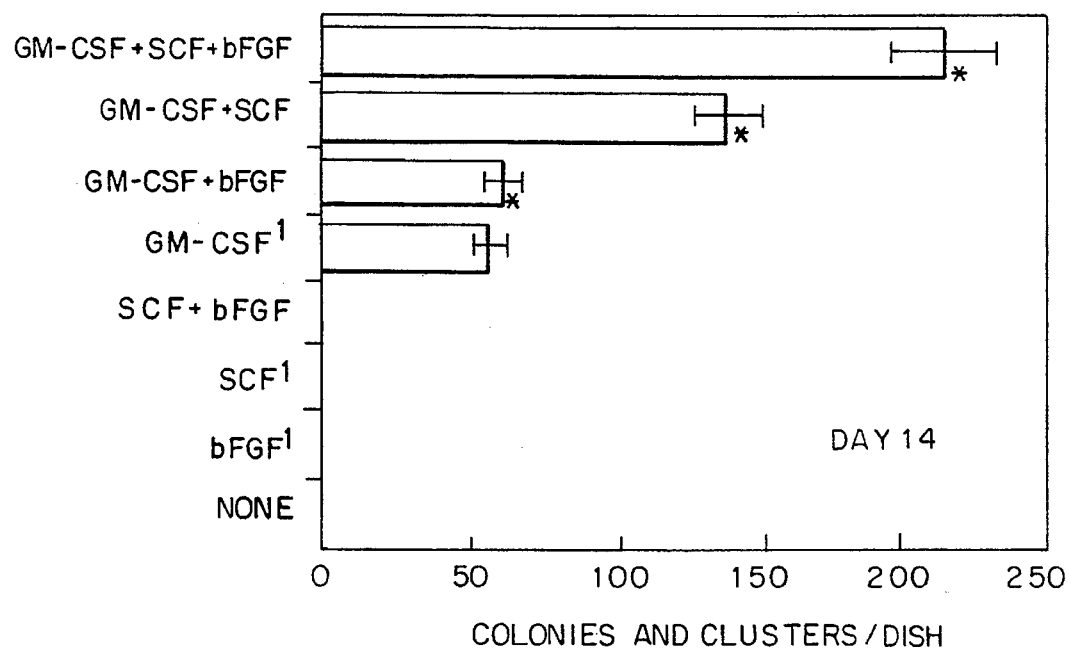

FIGS. 16A–16B present a graphical representation of the response of low density bone marrow cells to bFGF, SCF and GM-CSF alone and in combination. Data represents the mean±the standard deviation for eight plates scored on day 7 and day 14, in a representative experiment. For these studies, 1×10$^5$ low density bone marrow cells were cultured for 7 and 14 days respectively.

FIGWS. 17A–17B are is a graphical representation of the response of CD34+ progenitor cells to bFGF, SCF and GM-CSF alone and in combination. The data represent the mean number of day 7 and day 14 clusters and colonies±standard deviation of four separate experiments. In these experiments eight plates, seeded with 5×10$^3$ CD34+ cells were scored for colony and cluster growth on day 7 and day 14 of culture.

These experiments demonstrate that bFGF is potent stimulator of cultured stem cells and has a synergistic effect with other growth factors.

EXAMPLE IV

Stimulation of Stem cells from Fetal Brain and Transplant into Animal models and Humans for treatment of Neurodegenerative diseases.

Multipotent neural crest cells are isolated and cultured according to Stemple and Anderson, *Cell,* 71:973–985 (1992), which is entirely incorporated herein by reference, with the modification that bFGF is added to the medium at concentration ranges from 5 to 100 ng/ml in 5 ng/ml increments. Neural crest cells so cultured are found to be stimulated by the presence of FGF in increasing concentrations above 1 or 5 ng/ml.

These experiments demonstrate that bFGF is a potent stimulator of cultured neural stem cells and has a synergistic effect in combination with one or more other growth factors, such as EGF or NGF.

All references cited herein are entirely incorporated by reference herein, including all data, tables, figures, cited references and text presented in the cited references.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention.

What is claimed is:

1. A method for in vitro proliferation of hematopoietic progenitor cells that are progenitors of mature blood or lymph cells comprising culturing the hematopoietic progenitor cells in a culture medium containing a hematopoietic progenitor cell proliferating effective amount of a fibroblast growth factor for a time sufficient to permit proliferation of the hematopoietic progenitor cells.

2. A method in accordance with claim 1, wherein said hematopoietic progenitor cells are obtained drom bone marrow.

3. A method according to claim 1, further comprising recovering the hematopoietic progenitor cells proliferated in said culturing step.

4. A method according to claim 1, wherein said fibroblast growth factor is selected from the group consisting of basic fibroblast growth factor, acidic fibroblast growth factor, an hst/K-fgf gene product, FGF-6, KGF, FGF-5 and int-2.

5. A method according to claim 1, wherein said fibroblast growth factor is a basic fibroblast growth factor.

6. A method according to claim 5 wherein said basic fibroblast growth factor is selected from the group consisting of a 17.5 kilodalton, a 22.5 kilodalton, a 23.1 kilodalton, and a 24.2 kilodalton fragment of said fibroblast growth factor, as determined by sodium dodecyl sulfate polyacrylamide gel electrophoresis.

* * * * *